(12) United States Patent
Strother et al.

(10) Patent No.: US 10,688,306 B2
(45) Date of Patent: Jun. 23, 2020

(54) PROGRAMMING SYSTEMS FOR DEEP BRAIN STIMULATOR SYSTEM

(71) Applicant: Deep Brain Innovations LLC, Cleveland, OH (US)

(72) Inventors: Robert Strother, Willoughby Hills, OH (US); Jonathan Sakai, Fairview Park, OH (US); Geoffrey Thrope, Shaker Heights, OH (US)

(73) Assignee: Deep Brain Innovations LLC, Cleveland, OH (US)

( * ) Notice: Subject to any disclaimer, the term of this patent is extended or adjusted under 35 U.S.C. 154(b) by 59 days.

(21) Appl. No.: 15/107,290

(22) PCT Filed: Dec. 23, 2014

(86) PCT No.: PCT/US2014/072112
§ 371 (c)(1),
(2) Date: Jun. 22, 2016

(87) PCT Pub. No.: WO2015/100306
PCT Pub. Date: Jul. 2, 2015

(65) Prior Publication Data
US 2017/0001022 A1    Jan. 5, 2017

Related U.S. Application Data

(60) Provisional application No. 61/920,154, filed on Dec. 23, 2013.

(51) Int. Cl.
*A61N 1/372* (2006.01)
*A61N 1/05* (2006.01)
*A61N 1/36* (2006.01)

(52) U.S. Cl.
CPC ....... *A61N 1/37247* (2013.01); *A61N 1/0534* (2013.01); *A61N 1/3606* (2013.01);
(Continued)

(58) Field of Classification Search
CPC ............ A61N 1/37247; A61N 1/36175; A61N 1/36178
See application file for complete search history.

(56) References Cited

U.S. PATENT DOCUMENTS 3,833,005 A    9/1974    Wingrove
4,338,945 A    7/1982    Kosugi
(Continued)

FOREIGN PATENT DOCUMENTS

CN    86102850 A    11/1987
EP    1145735        10/2001
(Continued)

OTHER PUBLICATIONS

ISA/US, International Search Report and Written Opinion prepared for PCT/US2014/072112, dated Apr. 16, 2015.
(Continued)

*Primary Examiner* — George R Evanisko
(74) *Attorney, Agent, or Firm* — McDonald Hopkins LLC

(57) ABSTRACT

The present technology provides a medical stimulation system having a clinical programmer configured to operate on a computational and memory device having a wireless communication device. The technology also provides a neurostimulator configured to wirelessly communicate with the clinical programmer. The neurostimulator also includes a pulse generator operatively coupled with an electrode by a lead. The pulse generator is configured to transmit an electrical signal comprising a repeating succession of non-regular pulse trains. Each pulse train includes a plurality of pulses having non-regular, non-random, differing inter-pulse intervals therebetween. The pulse trains repeat in succession to treat a neurological condition. Further, the pulse trains are initiated by instructions communicated by the clinical programmer.

5 Claims, 14 Drawing Sheets

(52) U.S. Cl.
CPC ..... *A61N 1/36064* (2013.01); *A61N 1/36067* (2013.01); *A61N 1/36071* (2013.01); *A61N 1/36082* (2013.01); *A61N 1/36096* (2013.01); *A61N 1/36128* (2013.01)

(56) References Cited

U.S. PATENT DOCUMENTS

| | | |
|---|---|---|
| 4,979,507 A | 12/1990 | Heinz |
| 5,018,524 A | 5/1991 | Gu |
| 5,073,544 A | 12/1991 | Seto |
| 5,095,904 A | 3/1992 | Seligman |
| 5,184,616 A | 7/1993 | Weiss |
| 5,226,413 A | 7/1993 | Bennett |
| 5,485,851 A | 1/1996 | Erickson |
| 5,716,377 A | 2/1998 | Rise |
| 5,724,985 A | 3/1998 | Snell et al. |
| 6,066,163 A | 5/2000 | Sasha |
| 6,560,487 B1 | 5/2003 | McGraw |
| 6,560,490 B2 | 5/2003 | Grill |
| 6,738,668 B1 | 5/2004 | Mouchawar |
| 6,879,860 B2 | 4/2005 | Wakefield |
| 6,934,580 B1 | 8/2005 | Osorio |
| 6,944,501 B1 | 9/2005 | Pless |
| 7,010,351 B2 | 3/2006 | Firlik |
| 7,191,014 B2 | 3/2007 | Kobayashi |
| 7,321,796 B2 | 1/2008 | Fink |
| 7,483,747 B2 | 1/2009 | Gilner |
| 7,949,397 B1 | 5/2011 | Wenzel |
| 7,970,477 B2 | 6/2011 | Loeb |
| 8,073,544 B2 | 12/2011 | Pless |
| 8,355,789 B2 | 1/2013 | Werder |
| 8,447,405 B2 | 5/2013 | Grill |
| 8,694,106 B2 | 4/2014 | Pless |
| 8,798,755 B2 | 8/2014 | Grill |
| 8,923,981 B2 | 12/2014 | Grill |
| 9,089,708 B2 | 7/2015 | Grill |
| 9,242,095 B2 | 1/2016 | Grill |
| 9,259,579 B2 | 2/2016 | Grill |
| 9,572,988 B2 | 2/2017 | Grill |
| 9,744,363 B2 | 8/2017 | Grill |
| 10,086,204 B2 | 10/2018 | Grill |
| 10,086,205 B2 | 10/2018 | Grill |
| 2002/0077670 A1 | 6/2002 | Archer |
| 2002/0177882 A1 | 11/2002 | Dilorenzo |
| 2003/0135248 A1 | 7/2003 | Stypulkowski |
| 2004/0158298 A1 | 8/2004 | Gliner |
| 2004/0243192 A1 | 12/2004 | Hepp |
| 2004/0249422 A1 | 12/2004 | Gliner |
| 2005/0060009 A1 | 3/2005 | Goetz |
| 2005/0222641 A1 | 10/2005 | Pless |
| 2005/0228453 A1 | 10/2005 | Havel |
| 2005/0228461 A1 | 10/2005 | Osorio |
| 2006/0015153 A1 | 1/2006 | Gliner |
| 2006/0017749 A1 | 1/2006 | McIntyre |
| 2006/0111759 A1 | 5/2006 | Hoyme |
| 2006/0212089 A1 | 9/2006 | Tass |
| 2007/0067004 A1 | 3/2007 | Boveja |
| 2007/0198066 A1 | 8/2007 | Greenberg |
| 2007/0288064 A1 | 12/2007 | Butson |
| 2008/0045775 A1 | 2/2008 | Lozano |
| 2009/0036949 A1 | 2/2009 | Kokones |
| 2009/0082640 A1 | 3/2009 | Kovach |
| 2009/0110958 A1 | 4/2009 | Hyde |
| 2009/0131993 A1 | 5/2009 | Rousso |
| 2009/0264954 A1 | 10/2009 | Rise |
| 2010/0042194 A1 | 2/2010 | Ayal |
| 2010/0121407 A1 | 5/2010 | Pfaff |
| 2010/0121416 A1 | 5/2010 | Lee |
| 2010/0152807 A1 | 6/2010 | Grill |
| 2010/0312303 A1 | 12/2010 | York |
| 2010/0331916 A1 | 12/2010 | Parramon et al. |
| 2011/0093041 A1 | 4/2011 | Straka |
| 2011/0106213 A1 | 5/2011 | Davis |
| 2011/0184486 A1 | 7/2011 | De Ridder |
| 2011/0196441 A1 | 8/2011 | Ryu |
| 2011/0270348 A1 | 11/2011 | Goetz |
| 2012/0004707 A1 | 1/2012 | Lee |
| 2012/0016435 A1 | 1/2012 | Rom |
| 2012/0290041 A1 | 11/2012 | Snell et al. |
| 2013/0006330 A1 | 1/2013 | Wilder et al. |
| 2013/0102919 A1 | 4/2013 | Schiff |
| 2013/0231715 A1 | 9/2013 | Grill |
| 2013/0345773 A1 | 12/2013 | Grill |
| 2014/0257428 A1* | 9/2014 | Zhu ............... A61N 1/36178 607/46 |
| 2014/0353944 A1 | 12/2014 | Grill |
| 2017/0361099 A1* | 12/2017 | De Ridder ......... A61N 1/36096 |
| 2018/0064944 A1* | 3/2018 | Grill ................. A61N 1/36067 |

FOREIGN PATENT DOCUMENTS

| | | |
|---|---|---|
| EP | 2766087 | 8/2014 |
| JP | 2008506464 A | 3/2008 |
| WO | WO2006019764 A2 | 2/2006 |
| WO | WO2010039274 | 4/2010 |
| WO | WO2014130071 A1 | 8/2014 |

OTHER PUBLICATIONS

SA/US, International Search Report and Written Opinion prepared for PCT/US2014/072112, dated Apr. 16, 2015.

International Preliminary Report on Patentability for PCT/US11/38416, dated May 3, 2012.

International Search Report/Written Opinion dated Dec. 7, 2011 in International Patent Application No. PCT/US11/38416.

International Search Report and the Written Opinion of the International Searching Authority, PCT/US2013/046183, Duke University, dated Oct. 4, 2013.

International Search Report and the Written Opinion of the International Searching Authority, PCT/US2012/059787, Duke University, dated Jan. 4, 2013.

International Preliminary Examination Report, PCT/US2009/05459, Duke University, dated Jan. 11, 2011.

International Search Report and the Written Opinion of the International Searching Authority, PCT/US2009/05459, Duke University, dated Dec. 3, 2009.

Extended European Search Report, Application No. 09818122.5-1652/2340078, Duke University, dated Aug. 2, 2013.

Rubin, Jonathan et al., High Frequency Stimulation of the Subthalamic Nucleus Eliminates Pathological Thalamic Rhythmicity in a Computational Model, Journal of Computational Neuroscience, vol. 16, pp. 211-235, 2004.

McIntyre, Cameron et al., Cellular Effects of Deep Brain Stimulation: Model-Based Analysis of Activation and Inhibition, J. Neurophysiol, vol. 91, pp. 1457-1469, 2004.

Birdno, Merrill Jay, Analyzing the Mechanisms of Action of Thalamic Deep Brain Stimulation: Computational and Clinical Studies, Ph. D. Dissertation, Department of Biomedical Engineering, Duke University, Durham, NC, USA, Aug. 2009.

Constantoyannis, Constantine, et al., Tremor Induced by Thalamic Deep Brain Stimulation in Patients with Complex Regional Facial Pain, Movement Disorders, vol. 19, No. 8, pp. 933-936, 2004.

Benabid, Alim et al., Long-term suppression of tremor by chronic stimulation of the ventral intermediate thalamic nucleus, The Lancet, vol. 337, pp. 403-406, Feb. 16, 1991.

Davis, Lawrence, Handbook of Genetic Algorithms, Van Nostrand Reinhold, NY, pp. 1-402, 1991.

Dorval, Alan et al., Deep Brain Stimulation Alleviates Parkinsonian Bradykinesia by Regularizing Pallidal Activity, J. Neurophysiol, vol. 104, pp. 911-921, 2010.

Fogelson, Noa et al., Frequency dependent effects of subthalamic nucleus stimulation in Parkinson's disease, Neuroscience Letters 382, 5-9, 2005.

Grefenstette, John, Optimization of Control Parameters for Genetic Algorithms, IEEE Transactions on Systems, Man, and Cybernetics, vol. SMC-16, No. 1, pp. 122-128, Jan./Feb. 1986.

Feng, Xiao-jiang et al., Optimal Deep Brain Stimulation of the Subthalamic Nucleus—a Computational Study, Journal of Computational Neuroscience, 23(3):265-282, Jan. 9, 2007.

(56) References Cited

OTHER PUBLICATIONS

Grill, W.M. et al., Effect of waveform on tremor suppression and paresthesias evoked by thalamic deep brain stimulation (dbs), Society for Neuroscience Abstract 29, 2003.

Kuncel, Alexis et al., Clinical Response to Varying the Stimulus Parameters in Deep Brain Stimulation for Essential Tremor, Movement Disorders, vol. 21, No. 11, pp. 1920-1928, 2006.

Kupsch, A. et al., The effects of frequency in pallidal deep brain stimulation for primary dystonia, J. Neurol 250:1201-1205, 2003.

Tinnerman, Lars et al., The cerebral oscillatory network of parkinsonian resting tremor, Brain, 126, pp. 199-212, 2003.

Limousin, Patricia et al., Effect on parkinsonian signs and symptoms of bilateral subthalamic nucleus stimulation, The Lancet, vol. 345, pp. 91-95, Jan. 14, 1995.

Brucker, David. et al., Improved Efficacy of Temporally Non-Regular Deep Brain Stimulation in Parkinson's Disease, Department of Biomedical Engineering, Duke University, Durham NC 27708-0281, pp. 1-34. 2012.

Extended European Search Report for Application 13875748.9 PCT/US2013046183, dated Mar. 9, 2016, European Patent Office, Germany.

International Searching Authority, US Patent Office; International Search Report and Written Opinion for PCT/US2014/038809, dated Dec. 15, 2014, 19 pages.

Feng et al. "Toward closed-loop optimization of deep brain stimulation for Parkinson's disease: concepts and lessons from a computational model." J. Neural Eng. 4 (2007) L14-L21. Feb 23, 2007.

So et al. "Relative contributions of local cell and passing fiber activation and silencing to changes in thalamic fidelity uring deep brain stimulation and lesioning: a computational modeling study". Comput Neurosci (2012) 32:499-519. Oct. 5, 2011.

Kent et al. "Instrumentation to Record Evoked Potentials for Closed-Loop Control of Deep Brain Stimulation". Conf Proc IEEE Eng Med Biol Soc. 2011; 2011: 6777-6780. doi:10.1109/IEMBS.2011.6091671.

Dorval et al. "Deep Brain Stimulation that Abolishes Parkinsonian Activity in Basal Ganglia Improves Thalamic Relay Fidelity in a Computational Circuit". Conf Proc IEEE Eng Med Biol Soc. 2009; 1: 4230. doi:10.11091 EMB5.2009.5333611.

European Patent Office, Supplementary European Search Report, EP14874436, dated Jan. 17, 2018.

European Patent Office, European Search Report, EP 17001653, dated Jan. 4, 2018.

\* cited by examiner

PROGRAMMING SYSTEMS FOR DEEP BRAIN STIMULATOR SYSTEM

CROSS-REFERENCE TO RELATED APPLICATIONS

This application claims priority to International Application No. PCT/US2014/072112, entitled "PROGRAMMING SYSTEMS FOR DEEP BRAIN STIMULATOR SYSTEM," filed on Dec. 23, 2014 and U.S. Provisional Application No. 61/920,154 entitled "PROGRAMMING SYSTEMS FOR DEEP BRAIN STIMULATOR SYSTEM," filed on Dec. 23, 2013, each of which is hereby incorporated by reference in its entirety.

FIELD OF USE

The present invention relates generally to a programming system for an implantable deep brain stimulator.

BACKGROUND

Deep Brain Stimulators (DBS) have been found to be successful in treating a variety of neurological conditions, including, without limitation, movement disorders. Generally, such treatment involves placement of a deep brain stimulator type lead into a targeted region of the brain through a burr hole drilled in the patient's skull, and the application of appropriate stimulation through the lead to the targeted region.

Presently, in DBS, beneficial (symptom-relieving) effects are observed primarily at high stimulation frequencies above 100 Hz that are delivered in stimulation patterns or trains in which the interval between electrical pulses (the inter-pulse intervals) is constant over time. The beneficial effects of DBS on motor symptoms are only observed at high frequencies, while low frequency stimulation may exacerbate symptoms. See Benabid et al., 1991, and Limousin et al., 1995. Thalamic DBS at less than or equal to 50 Hz increases tremor in patients with essential tremor. See Kuncel et al. 2006. Similarly, 50 Hz DBS produces tremor in pain patients receiving simulation of the ventral posterior medial nucleus of the thalamus (VPM), but the tremor disappears when the frequency is increased. See Constantoyannis 2004. Likewise, DBS of the subthalamic nucleus (STN) at 10 Hz worsens akinesia in patients with Parkinson's disease (PD), while DBS at 130 Hz leads to significant improvement in motor function See Timmermann et al. 2004, and Fogelson et al. 2005. Similarly, stimulation of the globus pallidus (GP) at or above 130 Hz significantly improves dystonia, whereas stimulation at either 5 or 50 Hz leads to significant worsening. See Kupsch et al. 2003.

Model studies also indicate that the masking of pathological burst activity occurs only with sufficiently high stimulation frequencies. See Grill et al. 2004, FIG. 1. Responsiveness of tremor to changes in DBS amplitude and frequency are strongly correlated with the ability of applied stimuli to mask neuronal bursting. See Kuncel et al. 2007, FIG. 2.

Although effective, conventional high frequency stimulation generates stronger side-effects than low frequency stimulation, and the therapeutic window between the voltage that generates the desired clinical effect(s) and the voltage that generates undesired side effects decreases with increasing frequency. Precise lead placement therefore becomes important. Further, high stimulation frequencies increase power consumption. The need for higher frequencies and increased power consumption shortens the useful lifetime and/or increases the physical size of battery-powered implantable pulse generators. The need for higher frequencies and increased power consumption requires a larger battery size, and frequent charging of the battery, if the battery is rechargeable. As the stimulator portion of the DBS may be implanted into a patient, access to the leads, stimulator and the entirety of the DBS is often very difficult.

Once implanted into a patient, altering the battery or altering the stimulation of the system may preferably be avoided as surgery may be required to achieve such. It is desirable to limit the number of times that the implanted system is removed from the patient as every instance of surgery provides inherent risks that should generally be avoided.

However, there may be overriding benefits to alter some of the parameters of the stimulation applied to the patient, which may require altering parts of the system. Therefore, there is a need to alter the parameters of the DBS without requiring explanting of the DBS from the patient or other surgery.

The stimulation applied to the targeted region may be altered to improve the performance of the treatment. For example, a pattern of stimulation may be altered so as to improve the efficiency of the battery of the DBS, improve the efficacy of the treatment or both. However, not every patient reacts the same way to the stimulation. Accordingly, there is a need to be able to alter and manage the application of the stimulation to a specific patient or to treat a specific neurological condition. Further, there is a need to have a system that is easy to use for a clinician and patient. Further still, there is a need for a system that is programmable to alter the application of the stimulation.

SUMMARY

The present technology relates to a programming system applicable to a DBS that applies stimulation to treat any applicable neurological condition. The Clinical Programmer (CP) may provide a mechanism for communication with an implantable DBS. The CP may allow communication between a computing device and a wireless communications system. The CP may allow for data such as DBS stimulation settings, usage, error logs, and other information to be transmitted to and from the CP via the wireless communication system.

In one aspect, the present technology provides a medical stimulation system having a clinical programmer configured to operate on a computational and memory device having a wireless communication device. The technology also provides a neurostimulator configured to wirelessly communicate with the clinical programmer. The neurostimulator also includes a pulse generator operatively coupled with an electrode by a lead. The pulse generator is configured to transmit an electrical signal comprising a repeating succession of non-regular pulse trains. Each pulse train includes a plurality of pulses having non-regular, non-random, differing inter-pulse intervals therebetween. The pulse trains repeat in succession to treat a neurological condition. Further, the pulse trains are initiated by instructions communicated by the clinical programmer.

In one embodiment, the first electrical signal comprises non-regular pulse trains.

In one embodiment, the second electrical signal comprises second non-regular pulse trains or in another embodiment both the first and second electrical signal comprises non-regular pulse trains.

In one embodiment, the neurological condition is one of Parkinson's Disease, Essential Tremor, Movement Disorders, Dystonia, Epilepsy, Pain, Obsessive Compulsive Disorder, Depression, and Tourette's Syndrome.

In one embodiment, the computational and memory device is selected from a tablet computer, a laptop, a smartphone, or another electronic device.

In one embodiment, the wireless communication device of the computational and memory device is selected from a 403 MHz radio transceiver, a 2.4 GHz personal area wireless network, and an ultra-low power ultra high frequency (UHF) wireless radio.

In one embodiment, the neurostimulator comprises a unique identifying characteristic.

In one embodiment, the clinical programmer wirelessly communicates with the neurostimulator by its unique identifying characteristic.

In one embodiment, the wireless communication is secured through the use of encryption, message authentication, message security, or a combination thereof.

In one embodiment, the clinical programmer is managed by an interactive user interface operated on the computational and memory device.

In one embodiment, the user interface includes an interactive progress line displaying a progression of tasks for the neurostimulator and an interactive status bar displaying information related to the current task, the interactive status bar. The status bar may include an advance button, a pulse stimulation button, an amplitude button, an advanced programming screen task button, and a save button. Further, the user interface may also include an advanced programming screen button, a stimulation on-off button, and a screen lock button.

In one embodiment, the progress line displays tasks includes: Patient Information, Electrode Mapping, Optimize Amplitude, Optimize Stimulation Factor, Program & Save, or a combination thereof.

In one embodiment, the progress line identifies the tasks as complete or incomplete.

In one embodiment, the progress line allows a user to select at least one task, in any desired order. In one embodiment, the preferred order is the order of completing the tasks as they appear on the progress line from left to right (or from right to left as the case may be).

In one embodiment, the at least one task may be Optimize Stimulation Factor, which allows the user to associate one or more pattern of stimulation with at least one patient selectable attribute. For example, in one embodiment, this may include reducing the Stimulation Factor to reduce the overall battery consumption of the neurostimulator. In another embodiment, this may include increasing the Stimulation Factor to increase the probability of reducing patient symptoms.

In one embodiment, the clinical programmer allows a user to adjust pulse duration values, stimulus amplitude values of the pulses, or a combination thereof.

In one embodiment, the markers may be set to indicate clinically significant pulse duration values, stimulus amplitude values, or a combination thereof. In one embodiment, the markers are set to indicate stimulation factor values or stimulus amplitude values.

In one embodiment, the technology also includes a patient controller operatively connected to the clinical programmer via the wireless communication device. The patient controller allows a user to execute a program automated by the clinical programmer through a device other than the computational and memory device. Further, in some embodiments there may be only the patient controller and neurostimulator. In one embodiment, the patient controller is separate from the computational and memory device.

In one embodiment, the pulse train repeats indefinitely.

In one embodiment, the pulse train repeats until another pulse train sequence is selected by the clinical programmer and/or the patient controller.

In one embodiment, a waveform shape of at least one of the pulses is different from a second pulse waveform shape of another of the pulses of the non-regular pulse train.

In one embodiment, an amplitude of at least one of the pulses is different from a second pulse amplitude of another of the pulses of the non-regular pulse train.

In one embodiment, each pulse of the plurality of pulses comprises a waveform that is either of monophasic, biphasic, or multiphasic.

In one embodiment, at least one of the pulses comprises a monophasic waveform.

In one embodiment, at least one of the pulses comprises a biphasic waveform.

In one embodiment, at least one of the pulses comprises a multiphasic waveform.

In one aspect, the present technology provides a method including the step of operating a clinical programmer on a computational and memory device having a wireless communication device configured to wirelessly communicate with a neurostimulator. The method also includes applying electrical current to targeted neurological tissue region according to instructions supplied to the neurostimulator through the use of the clinical programmer. The electrical current includes a non regular pulse train comprising a plurality of pulses having non-regular, non random, differing inter-pulse intervals therebetween. The method may also include repeating the applying step in succession to treat a neurological condition.

In one aspect, the present technology provides a medical stimulation system having a clinical programmer configured to operate on a computational and memory device having a wireless communication device. The technology also includes a neurostimulator configured to wirelessly communicate with the clinical programmer. The neurostimulator may include a pulse generator operatively coupled with an electrode by a lead. The pulse generator may be configured to transmit an electrical signal comprising a repeating succession of non-regular pulse trains. Each pulse train may include a plurality of pulses having non-regular, non-random, differing interpulse intervals therebetween. The pulse trains may be programmed into the neurostimulator by instructions and data communicated by the clinical programmer. The pulse trains may modify a state of a patient. Still further in some embodiments, the pulse trains may be regular.

BRIEF DESCRIPTION OF THE DRAWINGS

Operation of the invention may be better understood by reference to the following detailed description taken in connection with the following illustrations, wherein.

DESCRIPTION OF THE PREFERRED EMBODIMENTS

Reference will now be made in detail to exemplary embodiments of the present invention, examples of which are illustrated in the accompanying drawings. It is to be understood that other embodiments may be utilized and structural and functional changes may be made without departing from the respective scope of the invention. Moreover, features of the various embodiments may be combined or altered without departing from the scope of the invention. As such, the following description is presented by way of illustration only and should not limit in any way the various alternatives and modifications that may be made to the illustrated embodiments and still be within the spirit and scope of the invention.

Figure 1:
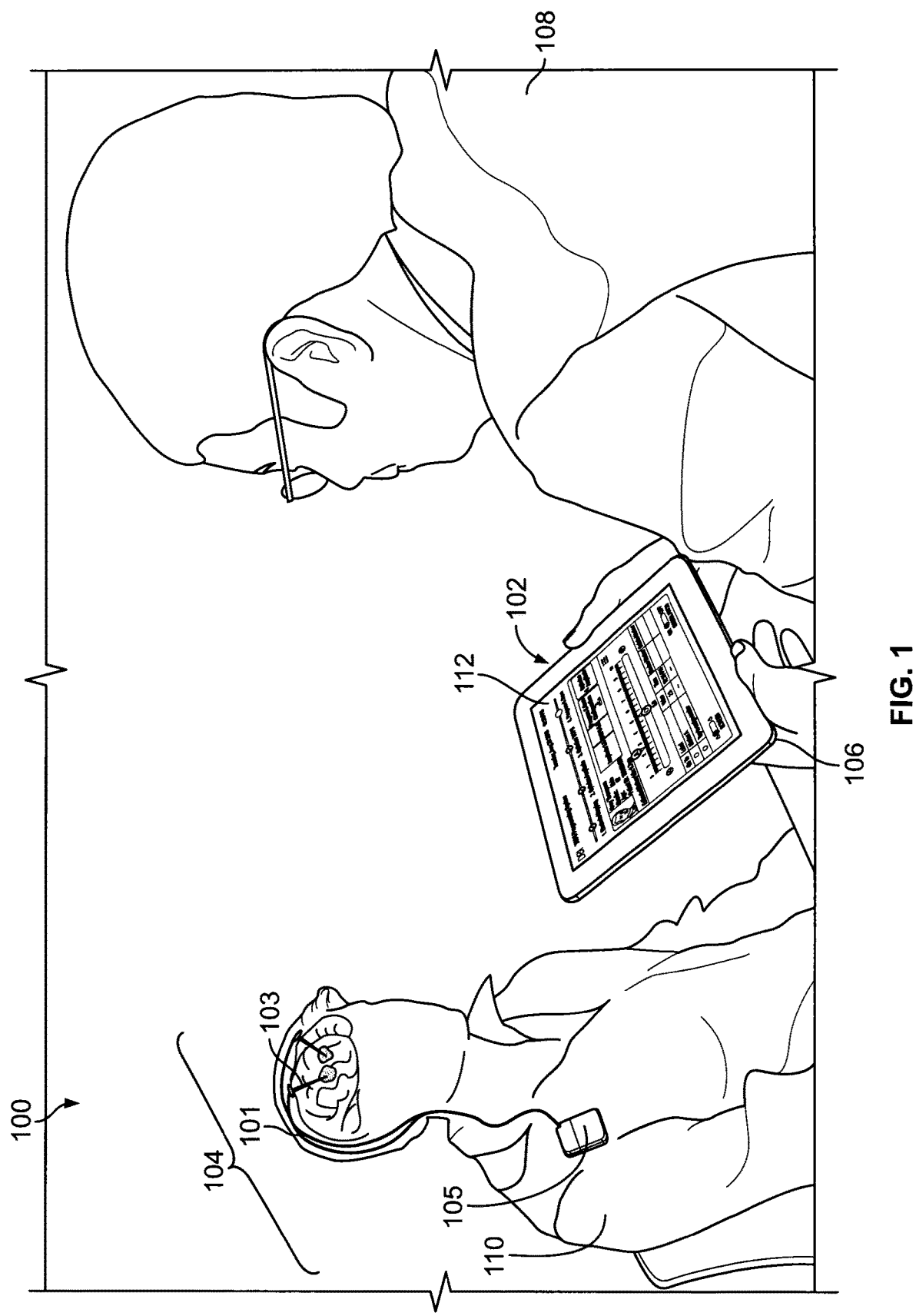
FIG. 1 is a perspective view of a user operating a clinical programmer of a DBS system on a patient.
Figure 2:
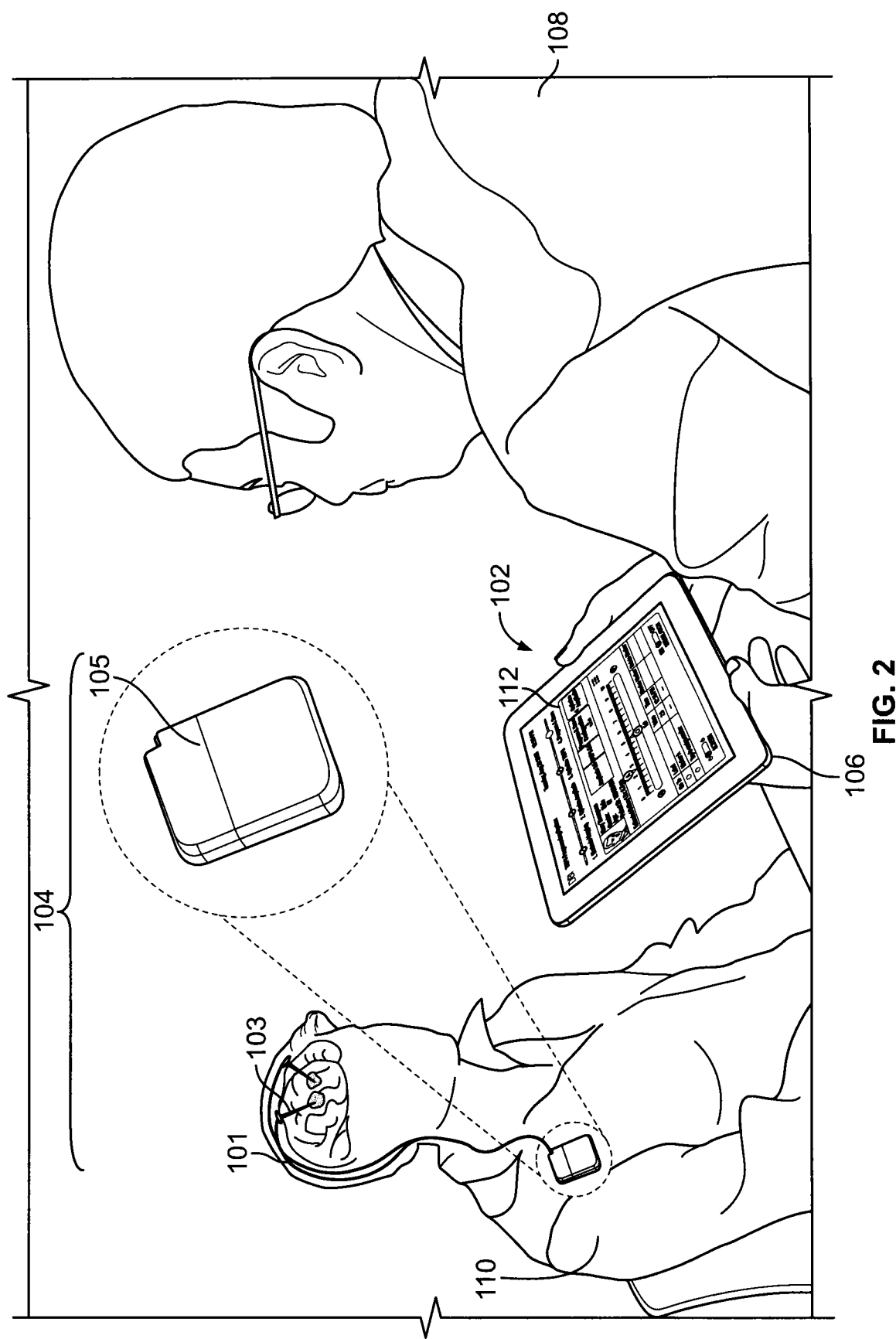
FIG. 2 is a perspective view of a user operating a clinical programmer for an implanted neurostimulator system on a patient.
Figure 3:
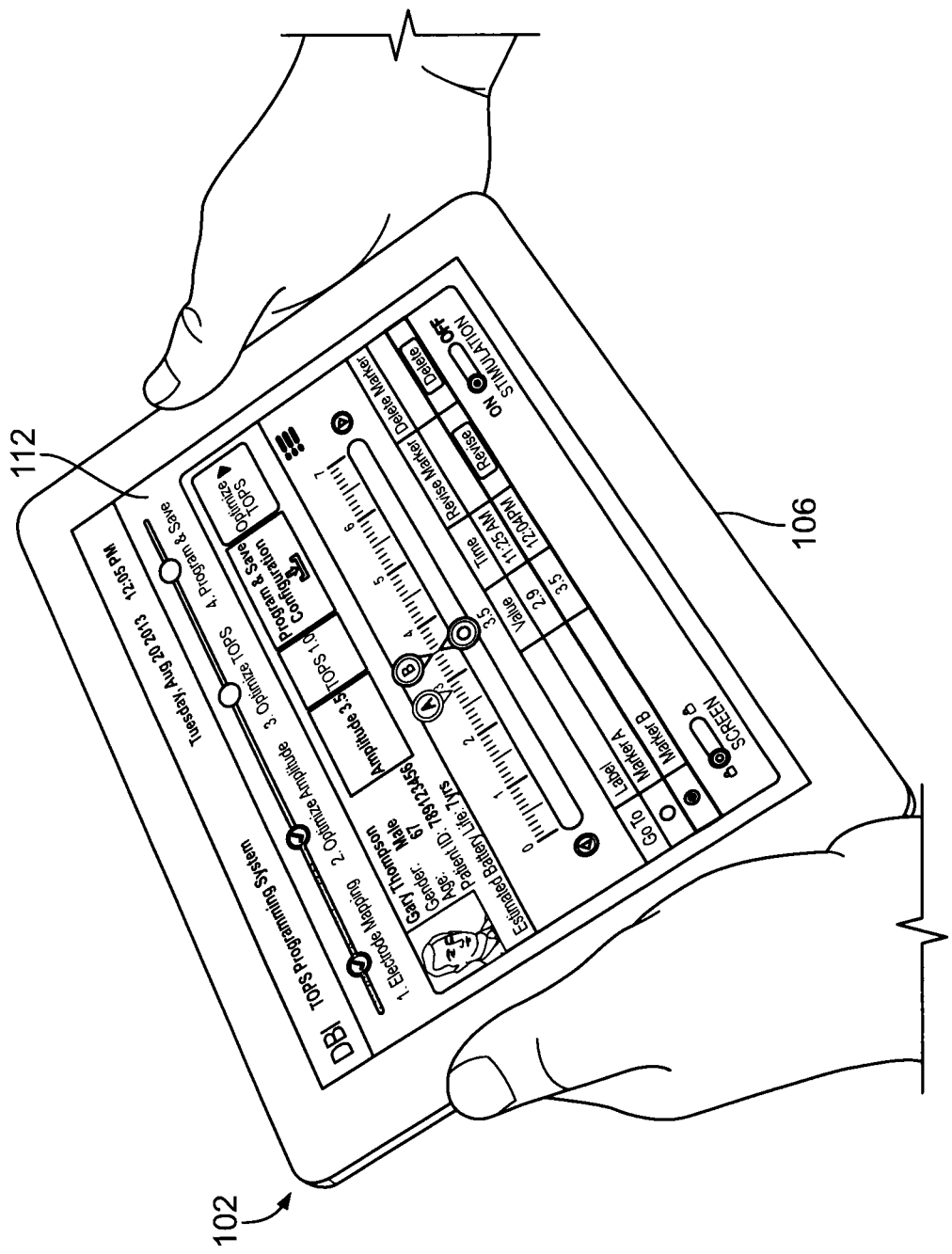
FIG. 3 is a perspective view of an embodiment of a clinical programmer.

As shown in FIGS. 1-3, the present technology generally comprises a deep brain stimulation (DBS) system 100 for stimulating tissues of the central nervous system. The system 100 may include a lead 101 placed in a desired position in contact with central nervous system tissue. In the illustrated embodiment, the lead 101 is implanted in a region of the brain, such as the thalamus, subthalamus, or globus pallidus for the purpose of deep brain stimulation. However, it should be understood, the lead 101 could be implanted in, on, or near the spinal cord; or in, on, or near a peripheral nerve (sensory or motor) for the purpose of selective stimulation to achieve a therapeutic purpose.

The distal end of the lead 101 carries one or more electrodes 103 to apply electrical pulses to the targeted tissue region. The electrical pulses are supplied by a pulse generator 105 coupled to the lead 101. The lead 101, electrodes 103, and pulse generator 105 are collectively referred to as a neurostimulator 104 for the purposes of this application. The neurostimulator 104 may be any appropriate type of fully or partially implantable neurostimulator capable of responsive treatment of neurological disorders through the use of stimuli, e.g., a Medtronic® neurostimulator, including but not limited to, RestoreSensor®, RestoreUltra®, RestoreAdvanced®, or PrimeAdvanced® neurostimulator.

In the illustrated embodiments, the pulse generator 105 of the neurostimulator 104 is implanted in a suitable location remote from the lead 101, e.g., in the shoulder region. It should be appreciated, however, that the pulse generator 105 could be placed in other regions of the body or externally.

When implanted, the case of the pulse generator 105 can serve as a reference or return electrode. Alternatively, the lead 101 can include a reference or return electrode (comprising a bi-polar arrangement), or a separate reference or return electrode can be implanted or attached elsewhere on the body (comprising a monopolar arrangement).

The pulse generator 105 may include an on-board battery to provide power. Currently, batteries must be replaced every 1 to 9 years, depending on the stimulation parameters needed to treat a disorder. When the battery life ends, the replacement of batteries requires another invasive surgical procedure to gain access to the implanted pulse generator. As will be described, the system 100 makes possible, among its several benefits, an increase in battery life by improved control of the stimulation parameters needed to treat a disorder. The pulse generator 105 may be configured to transmit an electrical signal comprising a repeating succession of pulse trains. Each pulse train may be non-regular pulse trains that include a plurality of pulses having non-regular, non-random, differing inter-pulse intervals therebetween. The pulse generator may be configured to transmit first and second electrical signals. In one embodiment, the first electrical signal comprises a first repeating succession of pulse trains. In one embodiment, the second electrical signal comprising a second repeating succession of pulse trains different from the first repeating succession of pulse trains. Either of the first or second repeating succession of pulse trains may be initiated by instructions communicated by the clinical programmer. In one embodiment, the first electrical signal comprises non-regular pulse trains. In another embodiment, the second electrical signal comprises second non-regular pulse trains.

The pulse trains may be programmed into the neurostimulator by instructions and data communicated by the clinical programmer. Still further in some embodiments, the pulse trains may be regular. The pulse trains, whether regular or non-regular, may modify a state of a patient.

The neurostimulator 104 is capable or receiving and transmitting messages via a wireless communication system as well as directed prescribed stimulation waveform patterns or trains through the lead 101 to the electrode(s) 103, which serve to selectively stimulate the targeted tissue region. Additionally, the neurostimulator 104 may have a unique identifying characteristic, e.g., a serial number.

The system 100 also includes a clinical programmer (CP) 102. By way of a non-limiting example, the CP 102 may include a computational and memory device of any appropriate configuration and type 106 (e.g., a tablet computer, a laptop, a smartphone, or another electronic device) comprising a wireless communication device operatively coupled with the implanted neurostimulator 104. The computational and memory device 106 comprises circuitry, a power source, e.g., a battery or a power cord, as well as a display for reviewing various screens of the CP 102. The display may be a touch-screen display, or it may be navigable by an attached or detached keyboard, a mouse, a stylus, voice recognition software, or any other appropriate means. The device 106 may also include sensors, cameras, microphones, an accelerometer, speakers, ports (e.g., USB port), etc.

FIGS. 1-3 show a user 108 operating the CP 102 on a tablet of any appropriate type and configuration 106 to apply predetermined stimulation parameters to a patient 110. The patient 110 may have a fully or partially implanted neurostimulator 104 that is wirelessly coupled with the CP 102 to treat a neurological condition. It should be understood, however, that the CP 102 and the neurostimulator 104 may be utilized to treat any appropriate neurological condition, including, but not limited to, Parkinson's Disease, Essential Tremor, Movement Disorders, Dystonia, Epilepsy, Pain, Obsessive Compulsive Disorder, Depression, and Tourette's Syndrome. It should be understood, therefore, that the teachings set forth herein are not limited to a specific neurological condition. Further, for purposes of this application, the user 108 may generally be a clinician. However, a user 108 may also be another caregiver, a family member, a friend, or the patient himself.

The neurostimulator 104 may be operatively connected to the CP 102 through the use of a wireless communication system (described below). The CP 102 is a tool that may be used for adjusting, evaluating, and programming stimulus patterns and parameters in the neurostimulator 104. The CP 102 may be of any appropriate configuration. By way of a non-limiting example, the CP 102 may include a computational and memory device 106 of any appropriate configuration and type (e.g., a tablet computer, a laptop, a smartphone, or another electronic device) comprising a wireless communication system operatively coupled with the implanted neurostimulator 104. As discussed above, the neurostimulator 104 may have a unique serial number, so that the CP 102 may provide wireless communications directed toward that particular neurostimulator 104 through the use of the unique serial number or any other manner of identifying itself. For example, the neurostimulator 104 may include data in a message sent to the CP 102 that identifies itself via a unique serial number. Similarly, messages sent from the CP 102 to the neurostimulator 104 may include data in a message header that identifies the serial number of the neurostimulator 104 to allow communications only to the desired neurostimulator 104. In one embodiment, one CP 102 could have the ability to contact multiple neurostimulators by directing separate messages to each unique neurostimulator serial number.

The CP 102 may include a user interface 112 that allows the user 108 to make changes to the stimulus of the neurostimulator 104. The user interface 112 may be of any appropriate configuration and is not limited to that shown and described herein. The majority of the user interface 112 may present information about and allow for the adjustment of parameters or features of a screen task or task. The user interface 112 may include several screens, each screen including easy to read and understand icons that may assist the user 108 with operation of the CP 102. The user interface 112 may be pre-programmed or may be programmed by a clinician or service provider such as to be customized. The user interface 112 may allow the user to obtain information from the neurostimulator 104 through wireless communications. During operation of the CP 102, the newly adjusted stimulus settings may be saved to a file and sent to the neurostimulator 104 or these operations may be performed at a later time in response to a user's action.

FIGS. 4-7 depict an exemplary organization of the user interface 112 of the CP 102. It should be understood, however, that this is merely an exemplary embodiment of the screen. The user interface 112 of the CP 102 may be of any appropriate configuration and is not limited to that shown and described herein. The user interface 112 may include more or less information than what is shown and described herein. Any appropriate amount and type of information may be included as is necessary. Further, the CP 102 may be programmable to remove or add information required or desired.

The user interface 112 may be a touch screen, may require use of a pointing device or mechanism such as a mouse, may be voice operated, or may be a combination of any of the above embodiments. A progress line 114 near the top of the user interface 112 may depict the progression of activities as a patient's neurostimulator 104 is programmed. The usual sequence of tasks on the progress line 114 may be shown going from left to right across the screen: Patient Information→Electrode Mapping→Optimize Amplitude→Optimize Stimulation Factor→Program & Save. In one embodiment, this is the preferred sequence of tasks. In other embodiments, the preferred sequence is completing the tasks in a different order than the sequence shown from left to right on the screen. The patient information may show on the progress line 114, but in some embodiments it may not show. The progress line 114 may appear consistently across multiple screens of the user interface 112. Alternatively, the progress line 114 may appear in different locations across multiple screens of the user interface 112. The progress line 114 may be interactive and allow the user 108 to select various tasks in the sequence to bring up a user interface 112 specific to that task, thereby advancing from one task to the next by clicking on various icons on the progress line 114. The progress line 114, therefore, allows the user 108 to see which tasks have been completed and which remain to be performed. Additionally, the progress line 114 allows the user 108 to complete the tasks in the order provided by the progress line 114 itself from left to right, to complete the tasks out of the usual order from left to right on the progress line 114, or to return and revise and/or repeat a past task.

In addition to the progress line 114, the user interface 112 may also contain a status bar 116. The status bar 116 may present information that is pertinent to the current stimulation program (e.g., the amplitude, the Stimulation Factor, or the frequency in conventional or fixed frequency stimulation, and the estimated battery life or recharge interval for a secondary cell neurostimulator). Additionally the status bar 116 may also indicate the goal of the parameters being applied to the patient, i.e., more efficiency (longer battery life) or more efficacy (better reduction in symptoms of the patient). The information may be presented in the same location along the status bar 116 at all times.

The two right-most buttons of the status bar 116 are buttons that may invoke actions. Specifically, the right-most button may be an advance button 118 that, when selected, advances the programming sequence to a new task. The button immediately to the left of the advance button 118 may be the save button 120. The save button 120 may allow, when selected, the programmed stimulus patterns and stimulus parameters to be saved; i.e., causes the patient's file inside of the CP 102 to update and allows those parameters to become the operational stimulus patterns and parameters of the neurostimulator 104.

If a programming session is terminated without selecting the save button 120, the user 108 may be warned that the stimulus parameters and patterns shown have not been saved. The user 108 may then be asked if he would like to save the stimulus parameters and patterns. Similarly, if the stimulus settings were saved, but then changed before the end of the session, the user 108 may be advised and asked if they want to save the revised settings.

In addition to presenting information about the current stimulation programmed, the other buttons of the status bar 116 may also be used to move between different tasks. For example, selecting an amplitude button 122 on the status bar 116 will cause an adjust amplitude screen task to be displayed. The user 108 may also navigate the CP 102 using the progress line 114 to move between various tasks. Additionally, the status bar 116 may include a Stimulation button 123. Selecting the Stimulation button 123 will cause an adjust Stimulation screen task to be displayed.

If an adjustment is made on the user interface 112, then that task on the progress line 114 may remain highlighted to remind the user 108 that an adjustment has been made on that item. Further, the status bar 116 may also remain highlighted for the same purpose.

Beneath the status bar 116 on the far right side of the user interface screen 112 is an advanced programming screen task button 124. Alternatively, the advanced programming screen task button 124 may be included directly in the status bar 116 or elsewhere on the user interface 112 in a consistent location. When selected, the advanced programming screen task button 124 moves the user 108 to an advanced programming screen task.

The advanced programming screen may allow the user 108 to review and revise the secondary stimulus parameters, e.g., the pulse duration of the stimulus, the choice of voltage or current control as the amplitude adjustment, and the frequency of the fixed frequency stimulation. The advanced programming screen may also allow the user 108 to set parameters as a default for different patients or patient populations/disease states as well as the current patient 110.

The advanced programming screen may also allow the user 108 to review the patient's usage of the neurostimulator 104; i.e., how much time stimulation was turned off, how much time stimulation was turned on, and the proportion of time spent in the various preprogrammed options. Additionally, the advanced programming screen may also allow the user 108 to restore the neurostimulator 104 to the configuration employed in the past (e.g., stimulus parameters and stimulus patterns) such as a factory or initial setting.

The CP 102 may use files or a database to store the information about each patient programmed. The stored information may include the type of implanted neurostimulator 104 used, as well as the serial number or other unique identifying number of the neurostimulator 104. The stored information may also include a history of stimulus patterns and parameters programmed and the history of patient usage of the DBS system 100. The usage history may be automatically retrieved from the neurostimulator every time the patient 110 is linked to the programmer by the user 108. Some of the information may only be stored in the CP 102 and/or in files that may be available for sharing with other clinicians through communications such as e-mail communications, websites, etc. This information may include personal background information about the patient 110, such as the patient's diagnosis, the patient's age, the patient's picture, the patient's age at diagnosis, the date a lead was implanted, etc.

In addition to being saved in the CP 102, this patient-specific data may also be stored on a secured web server accessed through the Internet. This may allow the patient's file to be accessed by a user using a CP different from the one originally used with the patient. The Internet cloud based storage may act like a shadow file system; i.e., when the original CP is being used, the cloud based file is updated when the CP saves a change to the file, but if a CP other than the original CP is being used, then the file is retrieved from the cloud at the beginning of the procedure and updated when the new CP file is saved.

The saved information may allow a new user 108 to view a patient's programmed history of stimulus patterns and parameters, as well as the usage history of the neurostimulator 104 by the patient 110. The CP 102 may advise the new user 108 if the other stimulus parameters are different than his default values. All the stimulus parameters and stimulus patterns retrieved may be saved in the new patient's file and/or database records. None of the patient's parameters may be changed without a specific action by the user 108 to change them.

When an already programmed patient 110 is linked to the CP 102, the values displayed by the CP (in the status bar 116 and on various screen tasks) may be the values currently in the neurostimulator 104.

Figure 4:
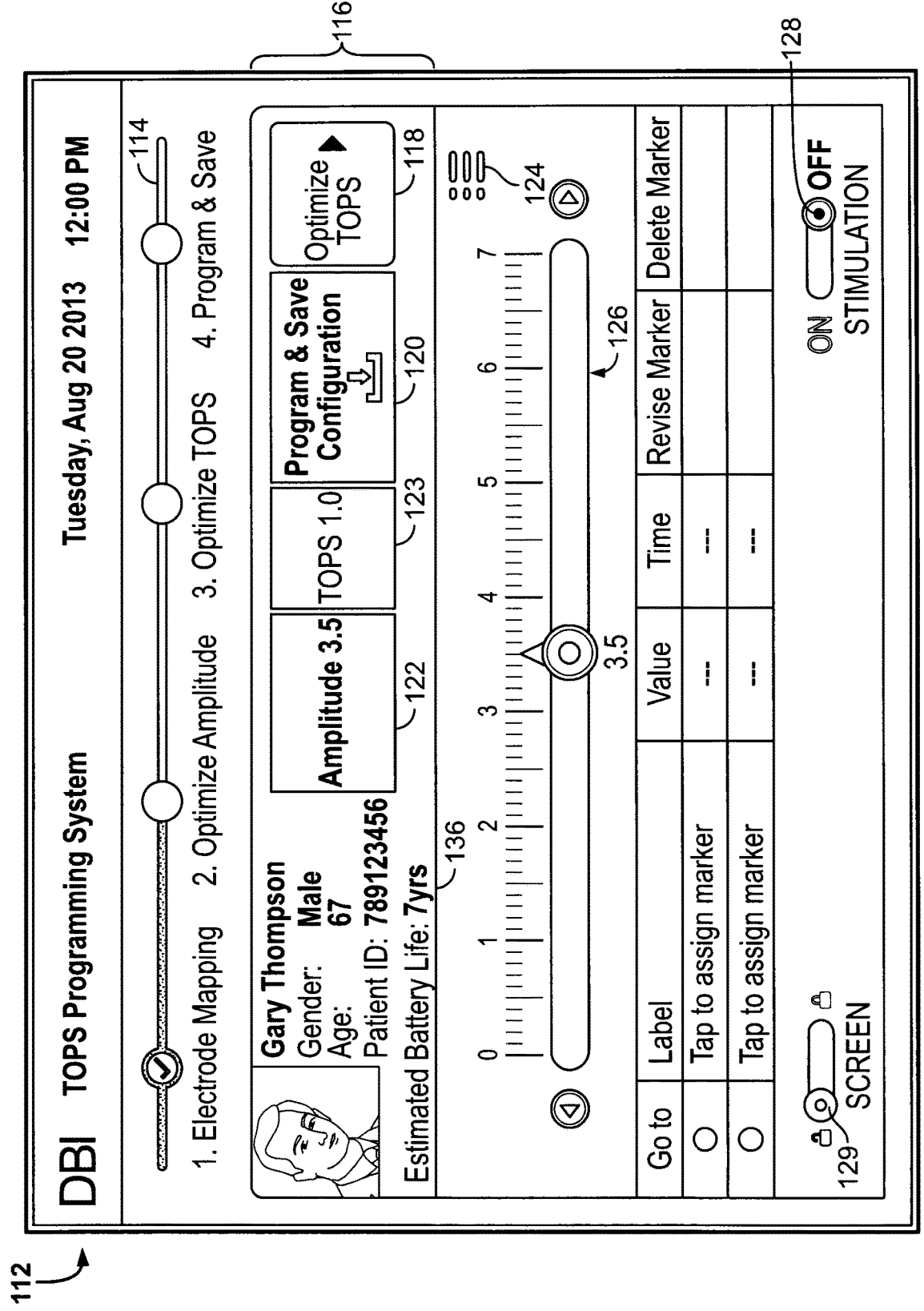
FIG. 4 is a view of an embodiment of a screen of the clinical programmer.

Each task on the user interface 112 may have the majority of the screen displaying the features or parameters of that task and may include controls to allow their adjustment. For example, the controls shown in FIG. 4 are slide controls 126. Rotary controls or horizontal or vertical slide controls may be utilized to adjust a screen task setting—any appropriate configuration of controls may be used without departing from the present teachings. Any control representation may be used provided it displays the present value or setting and displays it in context to the range (i.e., minimum and maximum values) available.

Figure 5:
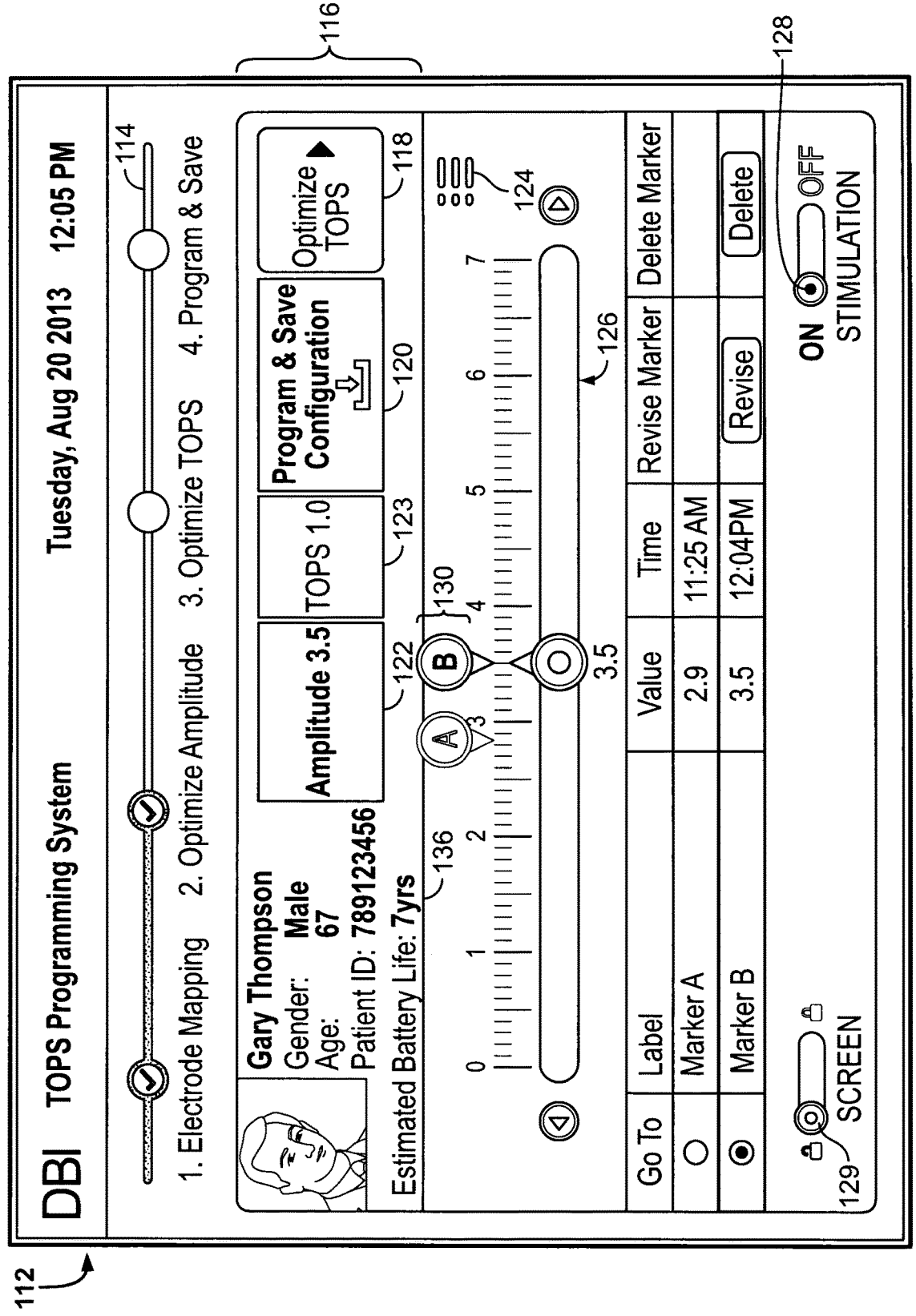
FIG. 5 is a view of a screen of the clinical programmer programming amplitude to the neurostimulator of the patient and utilizing a marker.

The slide control 126 shown in FIGS. 4 and 5 may be utilized to adjust the stimulus amplitude. The value of parameter set by the slide control may be adjusted by moving the value along the slide control to another value. This may be accomplished by dragging the slide control, or by touching or selecting a different value on the scale. Alternatively, a value may also be entered through typing on a keyboard, or by any other appropriate manner.

The stimulus parameters and patterns may be adjusted while the stimulus is being provided to the patient 110 in real time. Alternatively, the user 108 may elect to turn off the stimulation, make a change and then turn the stimulation back on. Every user interface 112 of the CP 102 that allows the user 108 to make changes to the stimulus pattern or stimulus parameters will also have the ability to start stimulation and stop stimulation through the use of a stimulation on-off button 128. The stimulation on-off button 128 is shown at the bottom right of corner of the user interface 112 of FIG. 4, but may be positioned on any appropriate location and is not limited to the configuration shown. For example, the stimulation on-off button 128 may be two separate virtual buttons, or it may be a virtual toggle switch. The stimulation on-off button 128 may always be located in the same position on the user interface 112 for consistency in user control. Alternatively, the stimulation on-off button 128 may be located in different locations on each user interface 112. Every user interface 112 may also have a screen lock 129 to prevent the tasks on the user interface from being adjusted if the CP 102 is switched to the "lock" position. The screen lock 129 may be two separate virtual buttons, or it may be a virtual toggle switch. The screen lock 129 may always be located in the same position on the user interface 112 for consistency in user control. Alternatively, the screen lock 129 may be located in different locations on each user interface 112.

In addition to allowing the slide control to adjust and set the value of the parameter being changed, the CP 102 may also allow for the setting of markers 130, such as shown in FIG. 5. A marker 130 may be a visual indication of a setting (e.g., sets of stimulus parameters/characteristics) that was significant to the user 108 during the programming process. For example, the markers 130 may be used to identify the lowest setting at which rapid improvement in symptom relief was no longer achieved by higher values, or the setting at which side effects became problematic, or any other appropriate characteristic identifier. In one embodiment, the markers may be set to indicate stimulation factors, stimulation frequencies, pulse duration values, stimulus amplitude values, or a combination thereof. In another embodiment, the markers may be set to indicate stimulation factor values or stimulus amplitude values.

Figure 6:
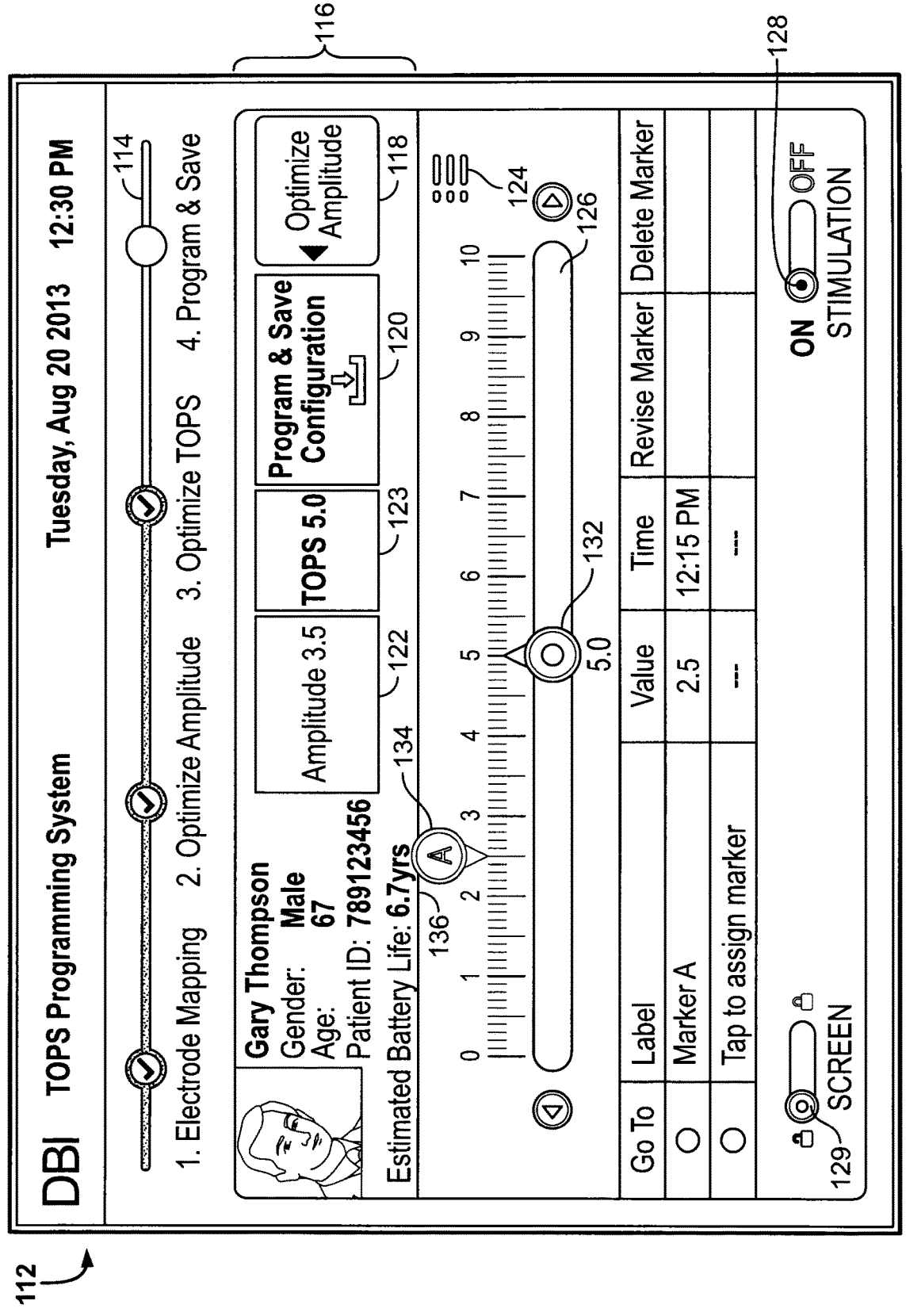
FIG. 6 is a view of a screen of the clinical programmer programming Temporally Optimized Patterns of Stimulation (TOPS) density or TOPS factor (hereinafter "Stimulation" factor) to the neurostimulator of the patient and utilizing a marker.

In one embodiment, markers 130 may be places on a user interface 112 to show a range of a single parameter. That is, the placement of markers 130 on a user interface 112 may allow the clinician to make subsequent choices about how to program the neurostimulator 104 and/or allow a patient 110 to be able to select their own treatment without the given range identified by the markers. For example, FIG. 6 shows the adjustment of the Stimulation Factor with a current setting 132 of 5.0 and a previously set marker 134 at 2.5.

Figure 7:
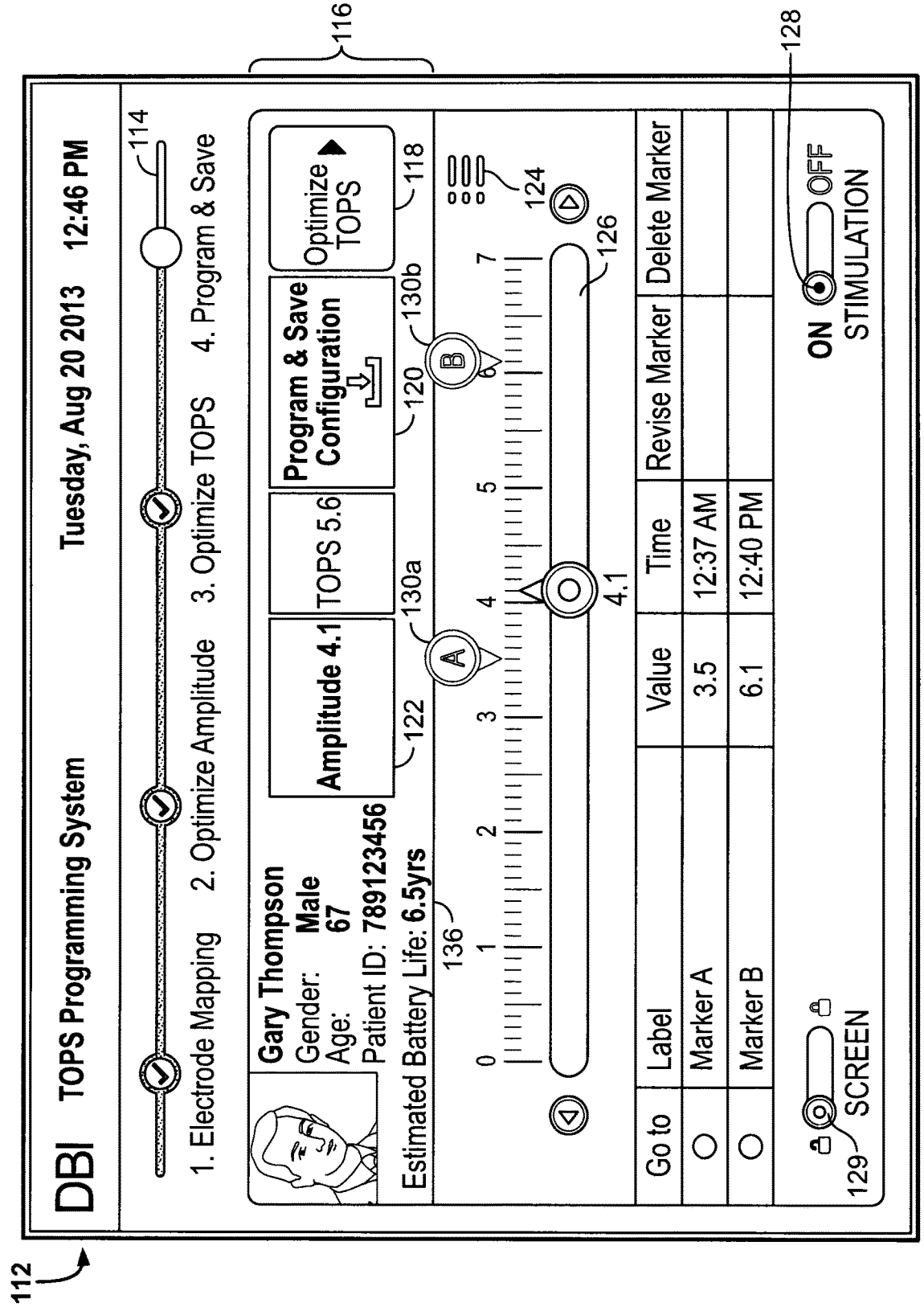
FIG. 7 is a view of a screen of the clinical programmer programming amplitude to the neurostimulator of the patient and utilizing two exemplary markers.

The typical uses of a marker 130 during the amplitude adjustment process, per FIG. 7, may include: a marker 130a assigned to the value at which the user 108 observes that further increases in amplitude yield relatively little further reduction of the symptoms; and another marker 130b assigned at the value at which the user 108 observes an unacceptable level of side effects. The markers 130 may be used to help the user 108 make informed choice about the appropriate value in an adjustment process.

The CP 102 may allow the patient 110 to select a different set of stimulus parameters of the implanted neurostimulator 104 to be adjusted to meet the patient's needs, such as for increased efficacy or increased efficiency. The CP 102 may be user friendly and easy for a user to operate. The CP 102 may implement TOPS and be used to adjust the pattern of stimulation to meet or otherwise address the patient's needs.

The CP 102 may also be used to adjust and program stimulation with a fixed frequency. Importantly, for both stimulation with the TOPS pattern and stimulation with a fixed frequency, the screen of the CP 102 indicated an Estimated Battery Life 136 (for a primary cell implant) or an Estimated Recharge Interval (for a secondary cell implant) for the stimulus parameters currently set and displayed. This allows the user 108 to include an understanding of the likely operating life of the implant when programming the patient's neurostimulator.

During operation of the CP 102, the newly adjusted stimulus settings may be saved to a file and sent to the neurostimulator 104 or these tasks may be performed at a later time in response to a user's action. The user interface 112 may allow the user 108 to obtain information from the neurostimulator 104, including, by way of a non-limiting example, the status of the battery inside the neurostimulator 104, the stimulus parameters or patterns currently programmed into the stimulator, and/or the usage history of a patient 110.

As discussed above, the CP 102 may include a computational and memory device of any appropriate configuration and type (e.g., a tablet computer, a laptop, a smart phone, or another electronic device) with a wireless communications link between the neurostimulator 104 and the CP 102. The wireless communications link may be an approximately 403 MHz radio transceiver, but is not limited to such. Any appropriate wireless communications link may be utilized, such as by way of a non-limiting example, a 2.4 GHz personal area wireless network such as Bluetooth® Low Energy or ANT (Dynastream Innovations Inc.: Garmin®).

Alternatively, or in addition, the wireless communications link may use any ultra-low power ultra high frequency (UHF) wireless radio (i.e., transverse electromagnetic radiation). The wireless communications link may be physically and electronically intrinsic to the CP circuitry or may be attached as a peripheral to the CP 102 (e.g., via USB). Similarly, an inductively coupled telemetry system may be used wherein a wand is placed above the skin over the neurostimulator.

Communication messages including, without limitation, actual data, such as stimulation settings, usage (compliance) and error logs, and other data may be transmitted to and from the CP 102 using a radio link, or any other appropriate method. Characters to detect or correct transmission errors, and characters to allow secure communications (e.g., authentication and authorization) may also be transmitted using the wireless communications link. By way of a non-limiting example, the transmission may be encrypted to protect against third party use. Additionally, other means of data privacy, security, and authentication may be used.

The CP 102 may configure the neurostimulator 104 for the desired stimulation (e.g., the voltage amplitude; the current amplitude; the distribution of current across, between, or among electrode surfaces including the case of the neurostimulator 104; the pulse duration; the frequency of a regular stimulus train; or the pulse-to-pulse intervals of a non-regular pattern of stimulation). Particularly, the CP 102 may configure the neurostimulator 104 to apply a non-regular electrical stimulation pattern as disclosed in U.S. Pat. No. 8,447,405. In one embodiment, the CP 102 can generate and send a number of patterns to be used by the neurostimulator 104 to generate the pulse timing, e.g., where each pattern is a sequence of pulse-to-pulse intervals and the sequence may repeat for a predetermined number of times before another pattern is selected. Alternatively, the CP 102 can generate and send a number of patterns to be used by the neurostimulator 104 to generate the pulse timing, e.g., where each pattern is a sequence of pulse-to-pulse intervals and the sequence may repeat indefinitely.

The CP 102 and the neurostimulator 104 may program and retain more than one stimulus pattern or set of parameters to allow the patient 110 to select different stimulus options based on their needs or the specifics of their symptoms at the time of use. The user 102 (including the patient 110) may make this selection using a patient controller (not shown) that may incorporate hardware for the wireless communications link. The patient controller may be operatively connected to the neurostimulator via the wireless communication device. The patient controller may allow a user to execute a program without use of the CP 102. In some embodiment, the program may be automated by the CP 102. The patient controller may employ, for example, an external device such as a small key fob like device or the patient controller may be a personal computer, laptop, tablet, smartphone, or the like, and is separate from the computational and memory device. Alternatively, the patient controller may be the CP 102. In some embodiments, there may be only the patient controller and neurostimulator in the system. The wireless communications link hardware may be inside the patient controller, or the hardware may be a separate unit that may operatively attach to the external device through a serial port connection. Alternatively, the hardware may be a separate unit with its own internal battery power that communicates with the patient controller through a standard unlicensed wireless communications link (e.g., Bluetooth® or Bluetooth® Low Energy), or by any other appropriate system. The hardware may then translate and re-transmit the messages on the wireless communications link used by the neurostimulator 104.

The wireless communications link between the neurostimulator 104 and the external patient controller may allow for a separation between the patient 110 and the patient controller. The patient controller may be held by a user 108 sitting across or near the patient 110 without the necessity of direct contact with the patient 110. The user 108 may program the neurostimulator 104 or a patient 110 may change the stimulus options himself. Additionally, the wireless communications link may also be used to communicate the status of a primary or secondary cell inside the neurostimulator 104 to the patient 110, user 108, or both. Further, the wireless communications link may also be used to communicate the usage history of the patient 110 (e.g., the quantity of options and duration of usage of each which were selected by the patient 110), or used to refine the strength of the high frequency (HF) magnetic field used to charge a secondary cell neurostimulator 104.

To minimize power consumption by the UHF receiver inside the neurostimulator, the neurostimulator 104 may only periodically search for incoming wireless communications. A potential downfall of this slow sampling rate may be the latency (or delay) between the message being ready to send and the message actually being sent and received by the neurostimulator. This sampling rate may be increased for several minutes (e.g., 1 to 30 minutes) after a qualified message has been received. This may allow subsequent messages during that interval (e.g., 1 to 30 minutes) to have a smaller latency. Alternatively, the neurostimulator 104 may also use the presence of a high frequency (HF) magnetic field or a static magnetic field (e.g., from a small permanent magnet) to start the interval of faster communications sampling by the neurostimulator.

Additional embodiments of the CP according the present teachings are described below. In the descriptions, all of the details and components may not be fully described or shown. Rather, the features or components are described and, in some instances, differences with the above-described embodiments may be pointed out. Moreover, it should be appreciated that these other embodiments may include elements or components utilized in the above-described embodiments although not shown or described. Thus, the descriptions of these other embodiments are merely exemplary and not all-inclusive nor exclusive. Moreover, it should be appreciated that the features, components, elements and functionalities of the various embodiments may be combined or altered to achieve a desired CP without departing from the spirit and scope of the present invention.

Figure 8:
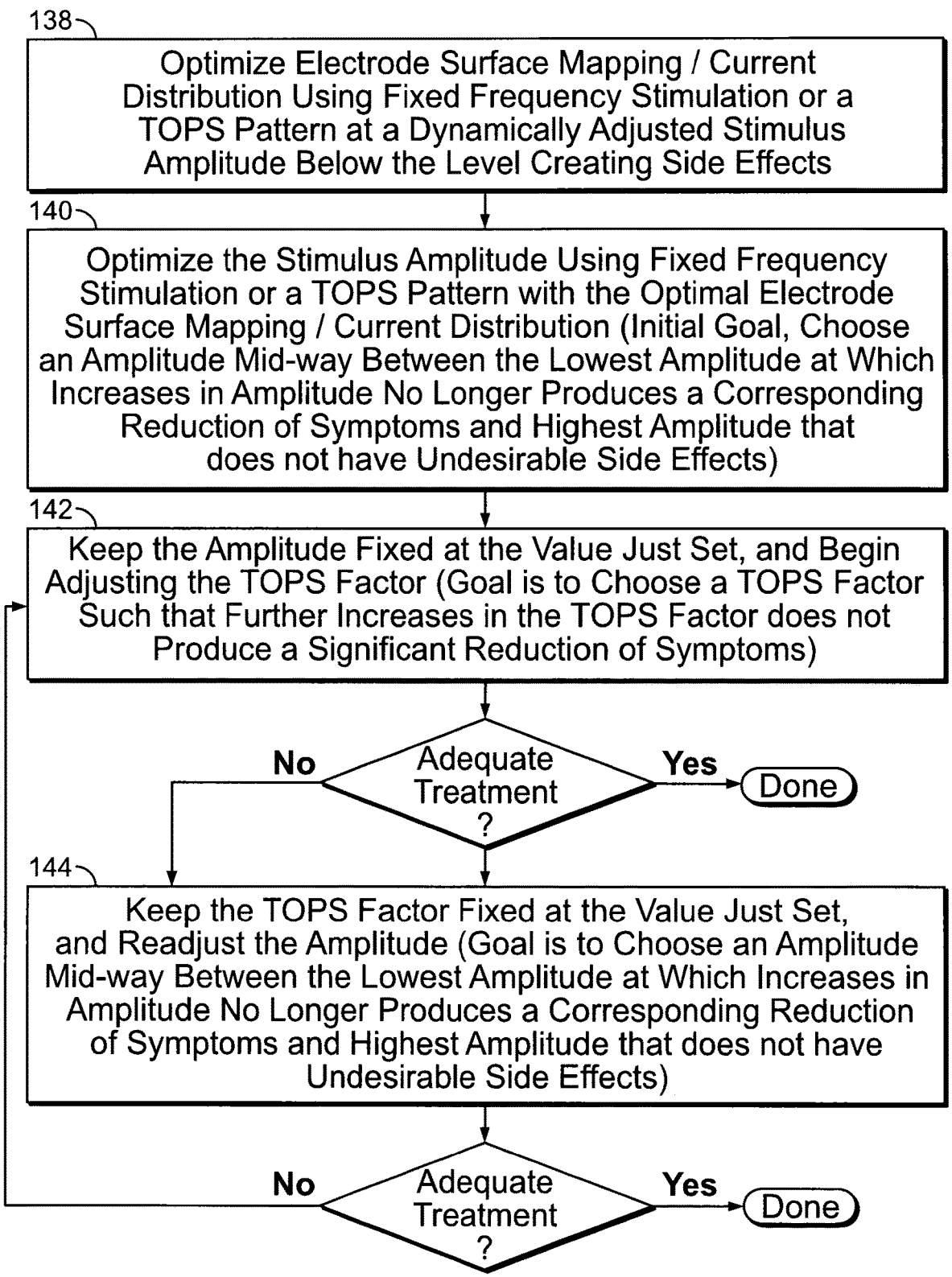
FIG. 8 is a flow chart identifying an embodiment of sequence for tuning a TOPS DBS process.

The sequence shown in FIG. 8 identifies an exemplary sequence for programming stimulation of the DBS system 100 with TOPS, examples of which are disclosed in U.S. Pat. No. 8,447,405, which is hereby incorporated by reference in its entirety.

The stimulation provided by the TOPS technology differs from conventional stimulation technology. The stimulation waveform pattern or train generated by the pulse generator 105 from input provided to the CP 1 differs from convention pulse patterns or trains in that the waveform comprises repeating non-regular (i.e., not constant) pulse patterns or trains, in which the interval between electrical pulses (the inter-pulse intervals or IPI) changes or varies over time. Compared to conventional pulse trains having regular (i.e., constant) inter-pulse intervals, the non-regular (i.e., not constant) pulse patterns or trains provide a lower average frequency for a given pulse pattern or train, where the average frequency for a given pulse train (expressed in hertz or Hz) is defined as the sum of the inter-pulse intervals for the pulse train in seconds ($\Sigma$IPI) divided by the number of pulses (n) in the given pulse train, or ($\Sigma$IPI)/n. A lower average frequency makes possible a reduction in the intensity of side effects, as well as an increase in the dynamic range between the onset of the desired clinical effect(s) and side effects, thereby increasing the clinical efficacy and reducing sensitivity to the position of the electrode(s). A lower average frequency brought about by a non-regular pulse pattern or train also leads to a decrease in power consumption, thereby prolonging battery life and reducing battery size.

The repeating non-regular (i.e., not constant) pulse patterns or trains can take a variety of different forms. For example, as will be described in greater detail later, the inter-pulse intervals can be linearly cyclically ramped over time in non-regular temporal patterns (growing larger and/or smaller or a combination of each over time); or be periodically embedded in non-regular temporal patterns comprising clusters or groups of multiple pulses (called n-lets), wherein n is two or more. For example, when n=2, the n-let can be called a doublet; when n=3, the n-let can be called a triplet; when n=4, the n-let can be called a quadlet; and so on. The repeating non-regular pulse patterns or trains can comprise combinations of single pulses (called singlets) spaced apart by varying non-regular inter-pulse intervals and n-lets interspersed among the singlets, the n-lets themselves being spaced apart by varying non-regular inter-pulse intervals both between adjacent n-lets and between the n pulses embedded in the n-let. If desired, the non-regularity of the pulse pattern or train can be accompanied by concomitant changes in waveform and/or amplitude, and/or duration in each pulse pattern or train or in successive pulse patterns or trains.

Each pulse comprising a singlet or imbedded in an n-let in a given train comprises a waveform that can be monophasic, biphasic, or multiphasic. Each waveform possesses a given amplitude (expressed, e.g., in amperes) that can, by way of example, range from 10 $\mu$a (E-6) to 10 ma (E-3). The amplitude of a given phase in a waveform can be the same or differ among the phases. Each waveform also possesses a duration (expressed, e.g., in seconds) that can, by way of example, range from 10 $\mu$s (E-6) to 2 ms (E-3). The duration of the phases in a given waveform can likewise be the same or different. It is emphasized that all numerical values expressed herein are given by way of example only. They can be varied, increased or decreased, according to the clinical objectives.

When applied in deep brain stimulation, it is believed that repeating stimulation patterns or trains applied with non-regular inter-pulse intervals can regularize the output of disordered neuronal firing, to thereby prevent the generation and propagation of bursting activity with a lower average stimulation frequency than required with conventional constant frequency trains, i.e., with a lower average frequency than about 100 Hz. This sequence may optimize the stimulus settings with the minimum of iterative re-adjustments.

The sequence shown in FIG. 8 identifies an exemplary sequence for programming stimulation of a DBS system with pulse stimulation—but the present teachings are not limited to this sequence. The sequence may be altered, i.e., steps may be done in a different order, steps may be skipped or steps may be added without departing from the present teachings. The sequence may begin by optimizing electrode surface mapping and current distribution through fixed frequency stimulation or pulse stimulation at a dynamically adjusted stimulus amplitude high enough to achieve symptom reduction and below the level creating side effects 138. The fixed frequency stimulation may be at a frequency the user 108 prefers; or it may be at a typical or usual value for the disease state or neurological condition being treated. Similarly, all stimulation may be at a pulse duration the user 108 prefers; or it may be at a typical or usual value for the disease state or neurological condition being treated. Subsequent adjustments of the pulse duration are only made in unusual conditions where the usual process is unsuccessful.

The sequence may continue by optimizing stimulus amplitude using fixed frequency stimulation or stimulation with a pulse stimulation pattern with the optimal electrode surface mapping 140. This may be accomplished by setting an initial goal, choosing an amplitude mid-way between the lowest amplitude at which increases in amplitude no longer produces a corresponding reduction of symptoms and the highest amplitude that does not have undesirable side effects. The amplitude should be kept fixed at this value and the user 108 may begin adjusting the TOPS factor (hereinafter "Stimulation factor"), i.e., the pulse stimulation pattern. The goal is to choose a Stimulation factor such that further increases in the Stimulation factor do not produce a significant reduction of the patient's symptoms 142. The Stimulation factor is a parameter that as its value increases from a minimum to a maximum, the temporal pattern of stimulation may vary in many ways; however, the average number of pulses per second may also increase from a minimum to a maximum.

The user 108 will then determine if this sequence is providing adequate treatment. If yes, the user 108 is done. If not, the user 108 should keep the TOPS factor fixed at the value just set, and readjust the amplitude 144. The goal is to choose an amplitude mid-way between the lowest amplitude at which increases in amplitude no longer produces a corresponding reduction of symptoms and highest amplitude that does not have undesirable side effects.

The user 108 may again determine if this sequence is providing adequate treatment. If yes, then the user 108 is done. If not, the user 108 may return to an earlier step in the sequence 142 or 144, e.g., adjusting the Stimulation factor, but typically more than one pass through this pathway may not be necessary to improve the quality of the treatment for the patient 110.

FIGS. 9-14 depicts an exemplary organization of a user interface 112 of the CP 102. It should be understood, however, that this is merely an exemplary embodiment of the screen.

Figure 9:
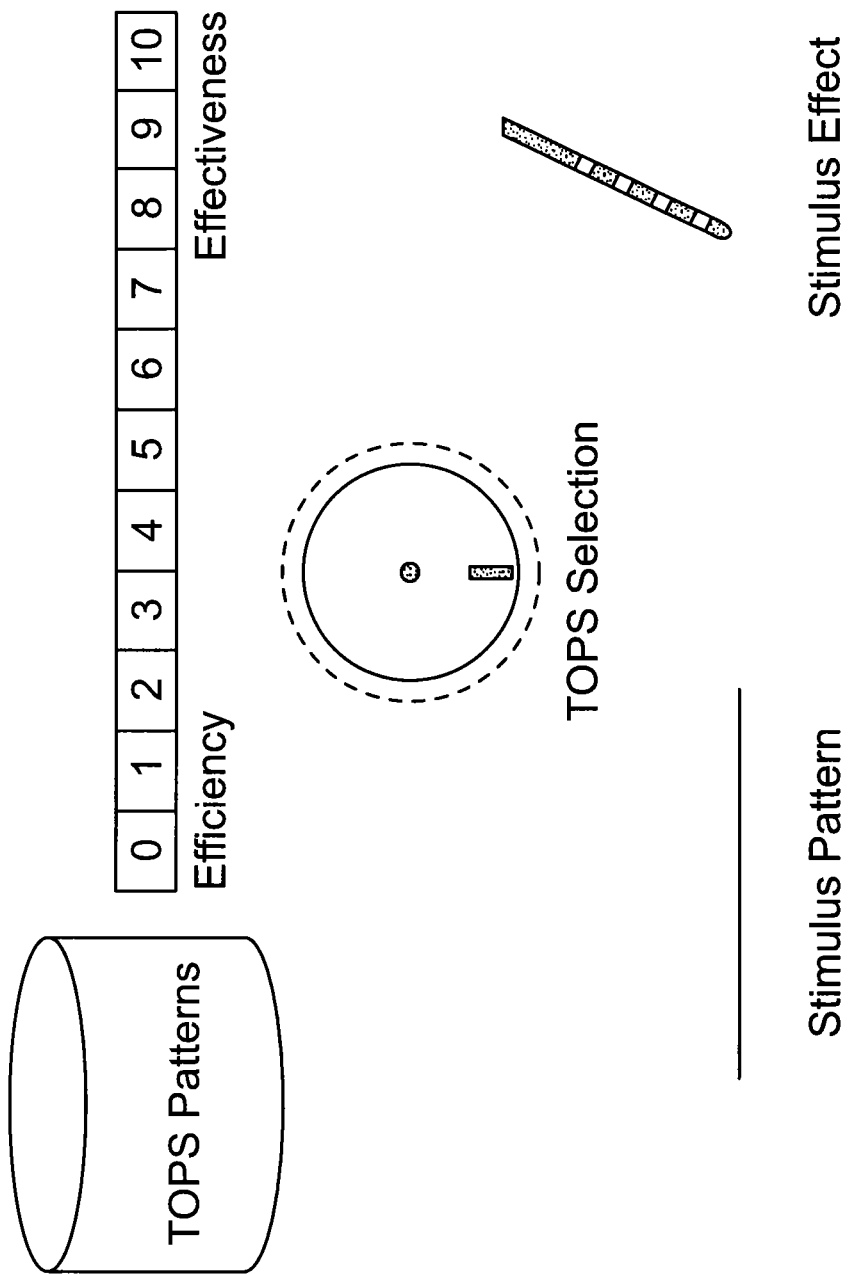
FIG. 9 is a view of a screen of a clinical programmer.
Figure 10:
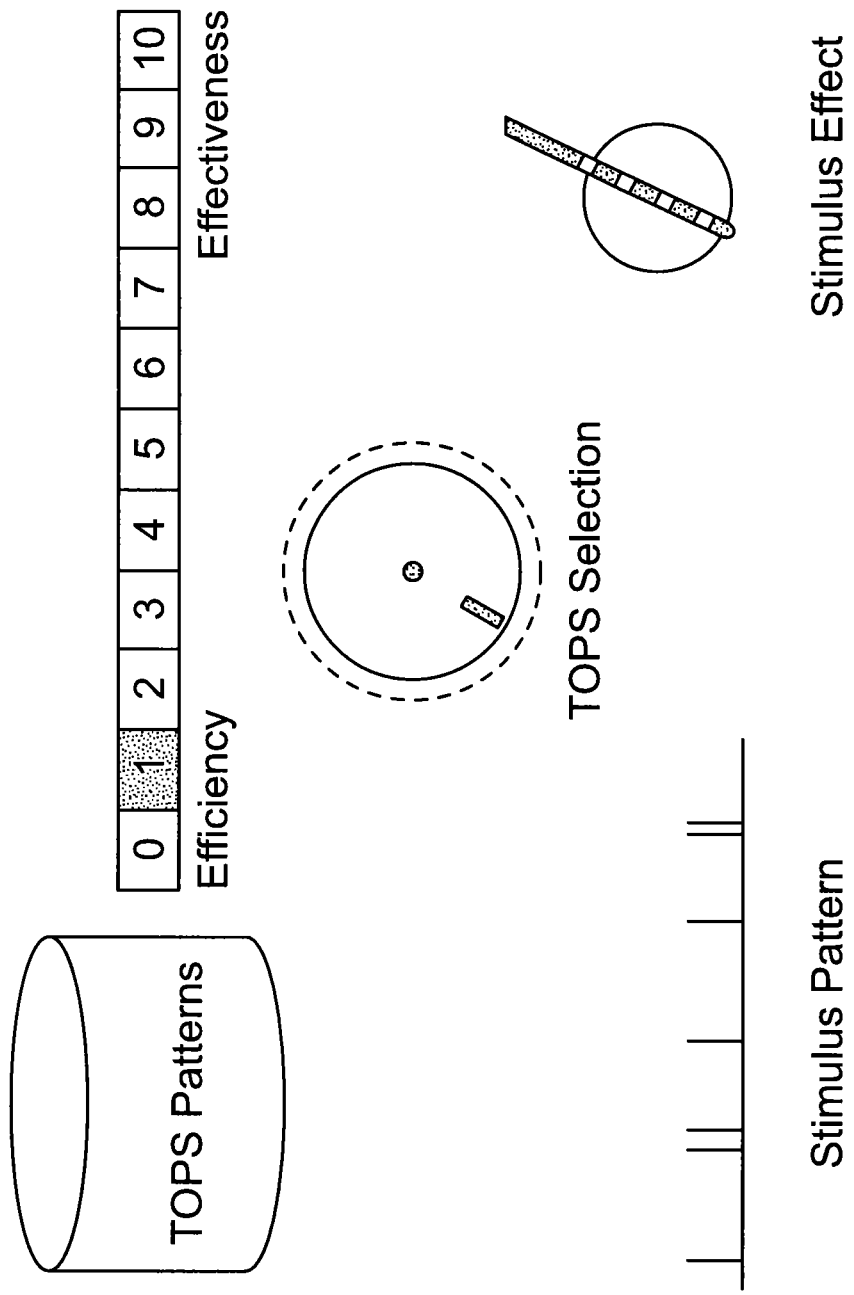
FIG. 10 is a view of a screen of the clinical programmer using TOPS to adjust the pattern to substantially maximize efficiency (i.e., minimize battery power consumption)
Figure 11:
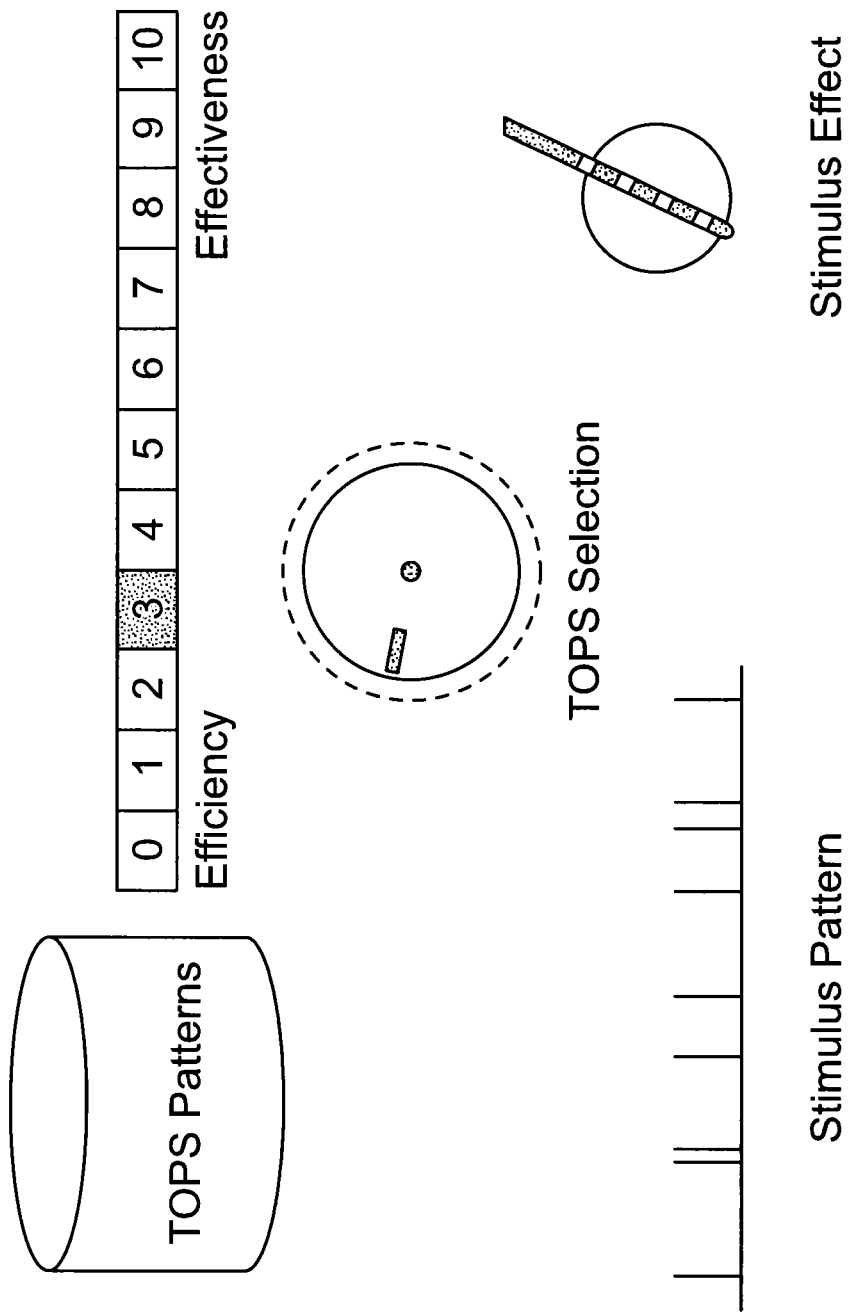
FIG. 11 is a view of a screen of the clinical programmer using TOPS to adjust the pattern to increase effectiveness.
Figure 12:
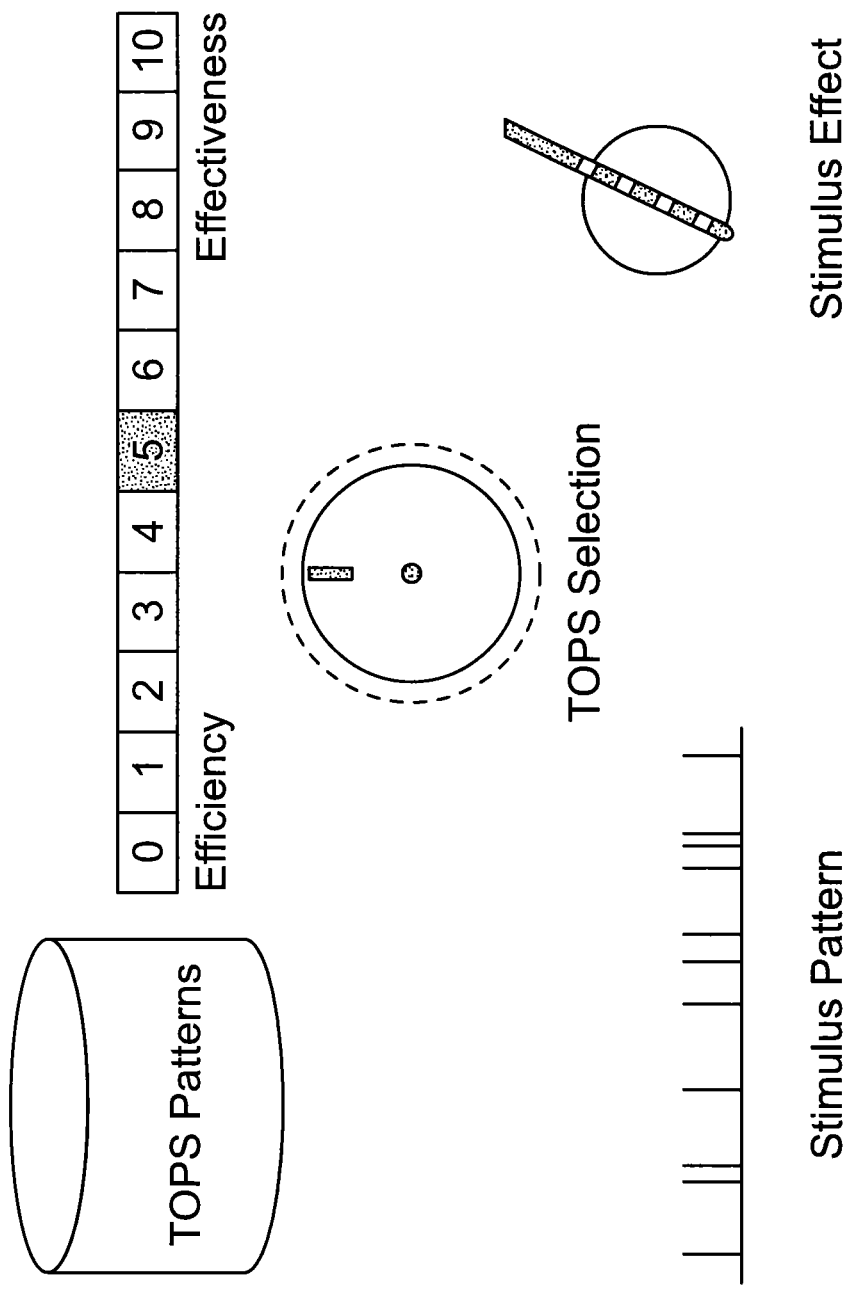
FIG. 12 is a view of a screen of the clinical programmer using TOPS to adjust the pattern to increase effectiveness.
Figure 13:
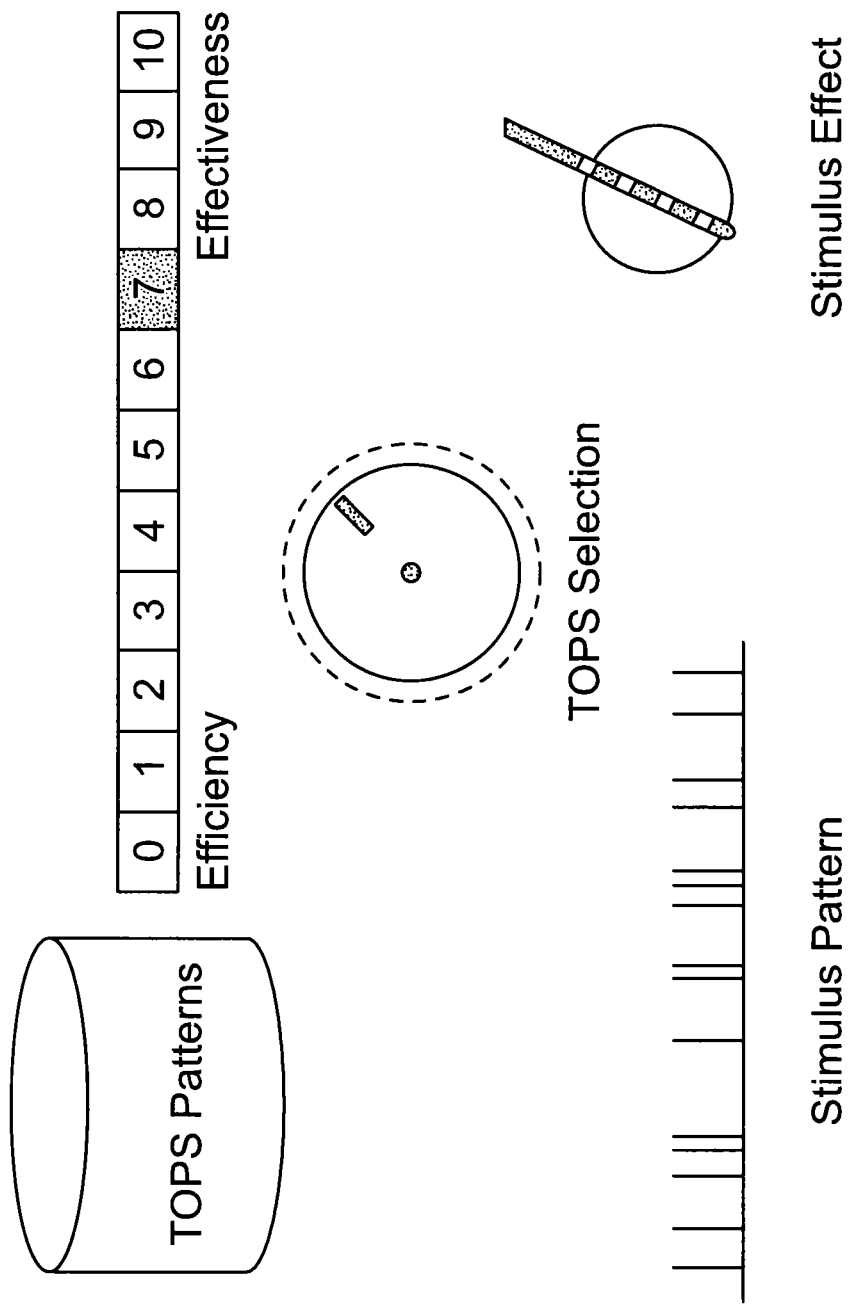
FIG. 13 is a view of a screen of the clinical programmer using TOPS to adjust the pattern to increase effectiveness.
Figure 14:
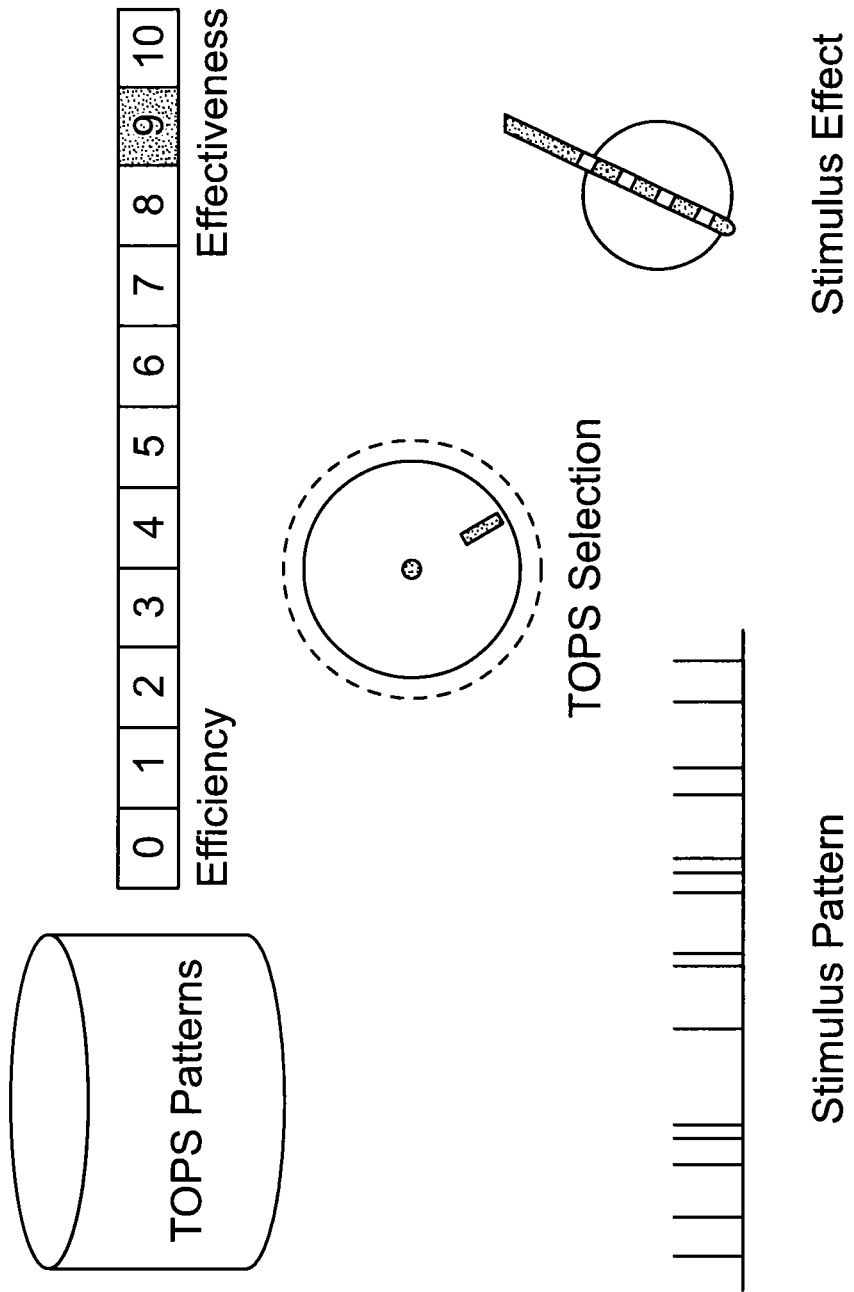
FIG. 14 is a view of a screen of the clinical programmer using TOPS to adjust the pattern to substantially maximize effectiveness (i.e., maximum reduction of residual symptoms).

FIG. 9 exemplifies a generic user interface 112. FIG. 10 exemplifies a setting to apply a pulse stimulation pattern for improved efficiency. FIG. 11 exemplifies a setting to apply a pulse stimulation pattern to improve effectiveness from FIG. 10. FIG. 12 exemplifies a setting to apply to pulse stimulation pattern to balance efficiency and effectiveness. FIG. 13 exemplifies a setting to apply a pulse stimulation pattern to improve effectiveness from FIG. 12. FIG. 14 exemplifies a setting to apply a pulse stimulation pattern to improve effectiveness from FIG. 13. It should be understood, however, that these screen representations are merely exemplary and not intended to be limiting. Any appropriate configuration may be used without departing from the present teachings. For example, the CP 102 allows the user 108 to associate one or more TOPS patterns and/or conventional stimulus parameters, with at least one patient selectable attribute/descriptor, e.g., low energy mode for sleep, highest efficacy (reduction of symptoms) for special patient events, etc. For example, in one embodiment, this may include reducing the Stimulation Factor to reduce the overall battery consumption of the neurostimulator. In another embodiment, this may include increasing the Stimulation Factor to increase the probability of reducing patient symptoms—or may include a combination of any of the foregoing. In one embodiment, the CP 102 may make use of a single control to adjust multiple, interrelated stimulus parameters and pulse timing patterns in a coordinated fashion to move along a desirable pathway of clinical effects. In another embodiment, a single control may select one of many pulse stimulation patterns as the control is adjusted from lowest power consumption (longest neurostimulator operating/service life) to the greatest power consumption (and shortest neurostimulator operating/service life). In yet another embodiment, a single control adjusts per pulse stimulus intensity by adjusting both stimulus amplitude and pulse duration in coordinated and clinically/physiologically desirable fashion.

Although the embodiments of the present invention have been illustrated in the accompanying drawings and described in the foregoing detailed description, it is to be understood that the present invention is not to be limited to just the embodiments disclosed, but that the invention described herein is capable of numerous rearrangements, modifications and substitutions without departing from the scope of the claims hereafter. The claims as follows are intended to include all modifications and alterations insofar as they come within the scope of the claims or the equivalent thereof.

Having thus described the invention, we claim:

1. A method comprising the steps of:
    operating a clinical programmer on a computational and memory device having a wireless communication device configured to wirelessly communicate with a neurostimulator;
    providing instructions: (a) to the neurostimulator through the clinical programmer, said instructions defining electrical current to include a non-regular pulse train consisting of a plurality of pulses having non-regular, non-random, differing inter-pulse intervals therebetween, and (b) by an interactive user interface operated on the computational and memory device;
    applying electrical current to targeted neurological tissue region according to the instructions;
    repeating the applying step in succession to treat a neurological condition;
  utilizing the clinical programmer to modify the electrical current;
  configuring the user interface to include:
    an interactive progress line displaying a progression of tasks for the neurostimulator;
    an interactive status bar displaying information related to the current task, the interactive status bar having at least one of:
    an advance button;
    a pulse stimulation button;
    an amplitude button;
    an advanced programming screen task button;
    a stimulation on-off button; and
    a save button;
    wherein the modified electrical current includes a second non-regular pulse train consisting of a plurality of pulses having non-regular, non-random, differing inter-pulse intervals therebetween that are different from the non-regular pulse train and wherein the displayed information also includes:
    an advanced programming screen button; and
    a screen lock button.

2. The method of claim 1, wherein the progression of tasks includes at least one item selected from:
Patient Information, Electrode Mapping, Optimize Amplitude, Optimize Stimulation Factor, and Program & Save.

3. The medical stimulation system of claim 2, wherein the configuring of the interface also includes an identification of each item in the progression of tasks as complete or incomplete.

4. The medical stimulation system of claim 3, wherein the configuring of the interface allows a user to select at least one task, in any desired order.

5. The method of claim 4, wherein the progression of tasks includes Optimize Stimulation Factor to associate one or more pattern of stimulation with at least one patient selectable attribute.

\* \* \* \* \*

UNITED STATES PATENT AND TRADEMARK OFFICE
CERTIFICATE OF CORRECTION

PATENT NO. : 10,688,306 B2
APPLICATION NO. : 15/107290
DATED : June 23, 2020
INVENTOR(S) : Robert Strother and Jonathan Sakai It is certified that error appears in the above-identified patent and that said Letters Patent is hereby corrected as shown below:

In the Claims

At Column 17, Line 6 and Line 10, In Claim 3 and 4 the phrase "medical stimulation system" should be deleted and replaced with the word --method--.

Signed and Sealed this
Twenty-third Day of May, 2023

Katherine Kelly Vidal
*Director of the United States Patent and Trademark Office*